(12) United States Patent
Perkins et al.

(10) Patent No.: US 10,613,073 B2
(45) Date of Patent: Apr. 7, 2020

(54) MICROFLUIDIC OPTICAL COMPUTING DEVICE

(71) Applicant: Halliburton Energy Services, Inc., Houston, TX (US)

(72) Inventors: David L. Perkins, The Woodlands, TX (US); Christopher Michael Jones, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 1030 days.

(21) Appl. No.: 14/426,689

(22) PCT Filed: Dec. 6, 2013

(86) PCT No.: PCT/US2013/073635
§ 371 (c)(1),
(2) Date: Mar. 6, 2015

(87) PCT Pub. No.: WO2014/171976
PCT Pub. Date: Oct. 23, 2014

(65) Prior Publication Data
US 2015/0212232 A1    Jul. 30, 2015

Related U.S. Application Data

(63) Continuation-in-part of application No. PCT/US2013/037227, filed on Apr. 18, 2013.

(51) Int. Cl.
*G01N 33/28* (2006.01)
*E21B 49/08* (2006.01)
*G01V 11/00* (2006.01)

(52) U.S. Cl.
CPC ........... *G01N 33/28* (2013.01); *E21B 49/087* (2013.01); *G01V 11/00* (2013.01)

(58) Field of Classification Search
CPC ........ G01N 33/28; E21B 49/087; G01V 11/00
USPC ...................................... 73/152.18
See application file for complete search history.

(56) References Cited

U.S. PATENT DOCUMENTS

| | | | |
|---|---|---|---|
| 6,822,454 | B2 | 11/2004 | Peck et al. |
| 7,305,306 | B2 | 12/2007 | Venkataramanan et al. |
| 7,788,972 | B2 | 9/2010 | Terabayashi et al. |
| 2009/0033933 | A1 | 2/2009 | Myrick et al. |
| 2009/0091320 | A1 | 4/2009 | Flaum et al. |
| 2009/0157315 | A1 | 6/2009 | Ong |
| 2012/0169334 | A1 | 7/2012 | Hopper et al. |
| 2012/0241643 | A1* | 9/2012 | Palmer ............... G01N 15/1436 250/428 |

(Continued)

FOREIGN PATENT DOCUMENTS

CA    2623793 A1    9/2009

OTHER PUBLICATIONS

International Search Report and the Written Opinion of the International Searching Authority, or the Declaration, dated Apr. 17, 2014, PCT/US13/7635, 19 pages, International Searching Authority, US.

(Continued)

*Primary Examiner* — John Fitzgerald
*Assistant Examiner* — Rodney T Frank
(74) *Attorney, Agent, or Firm* — Haynes and Boone, LLP

(57) ABSTRACT

Various embodiments of microfluidic optical computing devices coupled with Integrated Computational Element cores are described.

20 Claims, 11 Drawing Sheets

(56) References Cited

U.S. PATENT DOCUMENTS

2013/0031964 A1* 2/2013 Tunheim ............... G01N 21/85
                                                    73/61.48
2013/0032339 A1   2/2013 Kalia et al.
2013/0032736 A1   2/2013 Tunheim et al.

OTHER PUBLICATIONS

Office Action for Canadian Patent Application No. 2,904,211 dated Apr. 6, 2016, 6 pages.
European Patent Office, Supplementary European Search Report, dated Oct. 13, 2016, 7 pages, Europe.

* cited by examiner

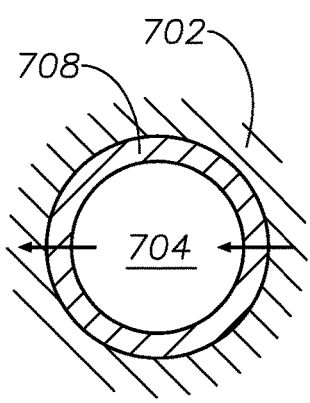
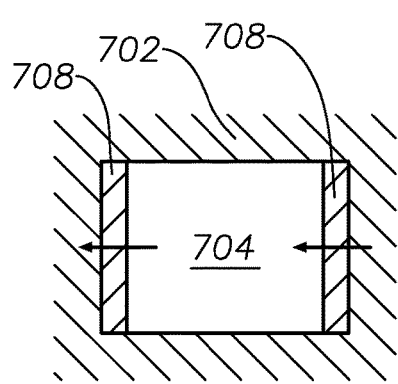
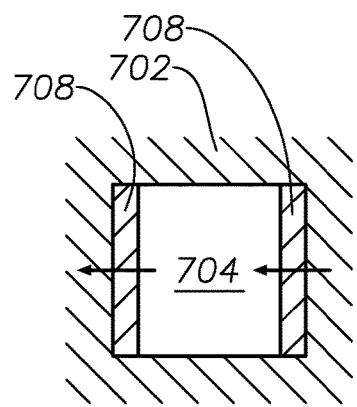
FIG. 8A    FIG. 8B    FIG. 8C
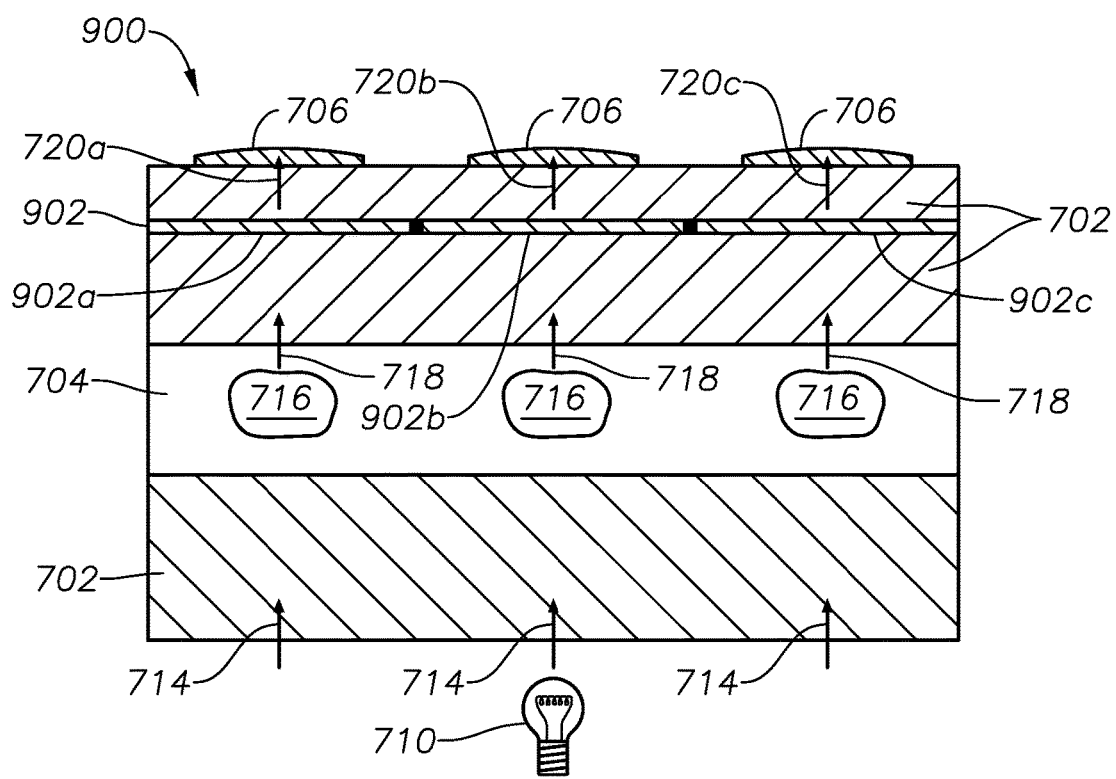
FIG. 9A

MICROFLUIDIC OPTICAL COMPUTING DEVICE

PRIORITY

The present application is a U.S. National Stage application of Patent Cooperation Treaty Application No. PCT/US2013/073635, filed on Dec. 6, 2013, which is a continuation-in-part of and claims priority to Patent Cooperation Treaty Application No. PCT/US13/37227, entitled "DEVICE AND METHOD FOR PARALLEL MICROFLUIDIC PRESSURE-VOLUME-TEMPERATURE ANALYSIS," filed Apr. 18, 2013, naming Christopher M. Jones et al. as inventors, the disclosures of which are hereby incorporated by reference in their entirety.

FIELD OF THE DISCLOSURE

Embodiments of present disclosure generally relate to fluid analysis and, more particularly, to a microfluidic optical computing device that utilizes Integrated Computational Elements to analyze fluid properties.

BACKGROUND

In the oil and gas industry, Pressure-Volume-Temperature ("PVT") experimentation is utilized to determine the phase behavior of reservoir fluids under various pressures, volumes, and temperatures. Such information is useful in deriving the economic value of a play, designing production strategies and managing production over the lifetime of an asset. PVT properties must be discovered to effectively manage an asset or collection of assets, including pipeline shipping.

Conventional PVT analysis, however, suffers from at least two drawbacks. First, the size of conventional PVT devices is too large for space-sensitive applications, such as downhole environments. Second, the time required to conduct conventional PVT experiments is too lengthy. A full PVT analysis usually takes days for a basic test to weeks for full testing. Particularly, it has taken months for some specialized PVT testing. Therefore, conventional PVT analysis has been limited downhole to a few simple rapid PVT-determined properties at single or limited pressure-temperature combinations close to wellbore conditions (which may not exactly match reservoir conditions).

Accordingly, in view of these drawbacks, there is a need in the art for a compact and versatile PVT analysis device which provides accurate data in a rapid fashion. This same device would also be useful in any other application necessitating the use of a compact fluid analysis device.

BRIEF DESCRIPTION OF THE DRAWINGS

FIGS. 8A-8C are cross sectional views of alternative geometries of the fluid channels according to certain illustrative embodiments of the present disclosure;

FIGS. 9A-9B are schematic sectional representations of a microfluidic optical computing device along line 7B of FIG. 7A, according to alternate illustrative embodiments of the present disclosure;

DESCRIPTION OF ILLUSTRATIVE EMBODIMENTS

Figure 1:
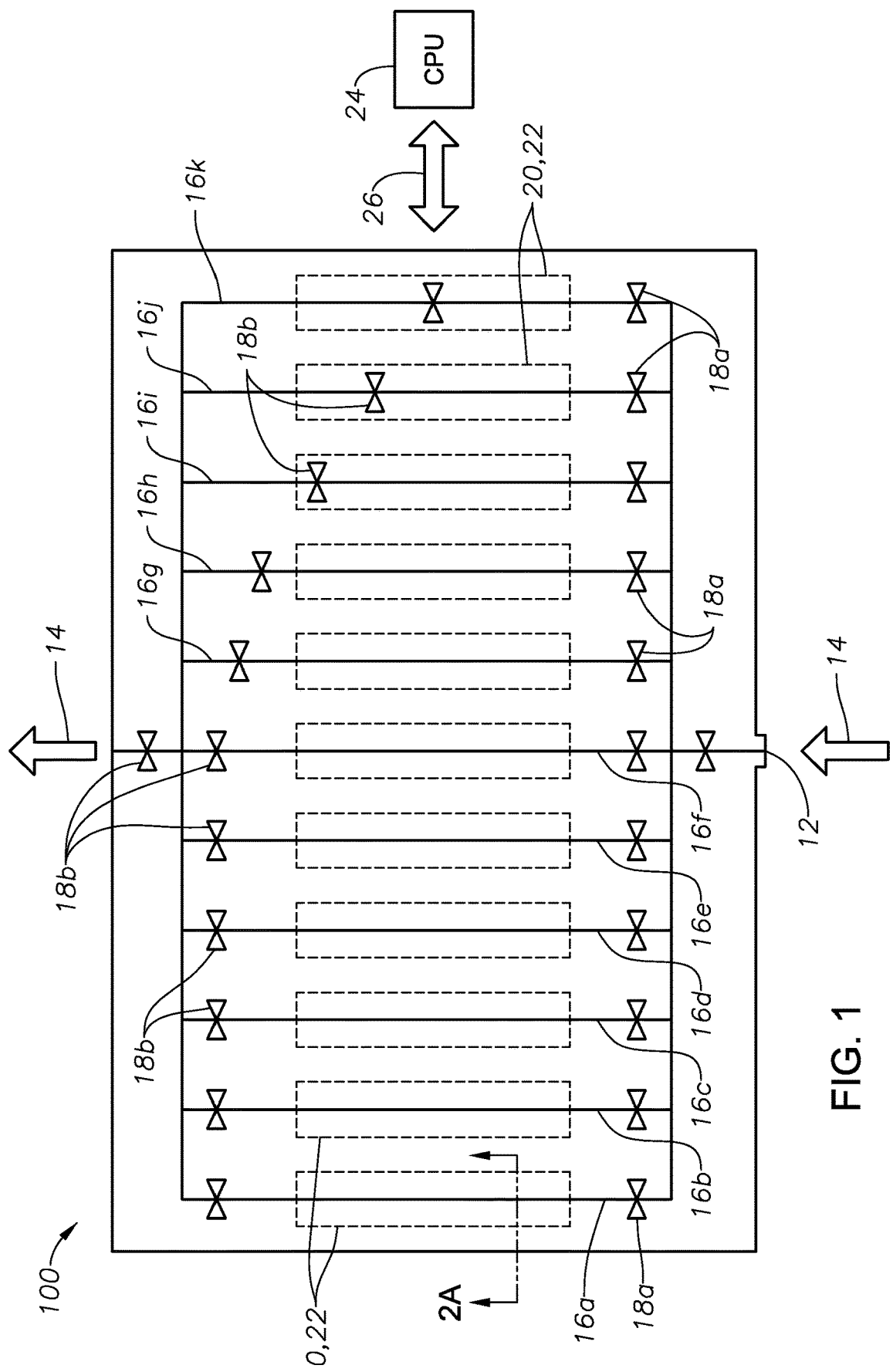
FIG. 1 illustrates a microfluidic device according to an illustrative embodiment of the present disclosure.

Illustrative embodiments and related methodologies of the present disclosure are described below as they might be employed in a microfluidic device coupled with a multivariate optical calculation device. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the disclosure will become apparent from consideration of the following description and drawings.

As described herein, the present disclosure is directed to microfluidic optical computing devices coupled with Integrated Computation Element cores, to thereby analyze various fluid samples in a variety of applications. In addition, the present disclosure is also directed to a microfluidic methods and device to parallelize a PVT analysis such that part of a pressure, temperature and volume combination is performed separately from others, thus providing a rapid PVT analysis. In one illustrative embodiment, a microfluidic cell, or chip, is designed to accept a small amount of fluid, separate the fluid into a number of sample volumes, and distribute the sample volumes to a plurality of parallel microfluidic channels (or columns). A nuclear magnetic resonance ("NMR")

apparatus is then utilized to determine the phase characteristics (amount of liquid, gas or solid) of the fluid sample volumes within in each microfluidic channel. The same or differing pressure, volume or temperature may be utilized in multiple microfluidic channels. Circuitry on-board, or remote from, the microfluidic device then utilizes the phase characteristic data to perform a variety of PVT experiments to derive phase behavior, transport property, bulk property, etc. In other illustrative embodiments, the phase characteristic data of each channel representing multiple pressure, temperature and volume point measurements is recombined statistically across PVT space with or without PVT point repeats for a complete PVT analysis, thus improving the accuracy over the repeated experiments occurring in the channels.

Accordingly, by dividing the fluid into a plurality of separate channels, the PVT analysis time is greatly reduced. If, for example, a complete prior art PVT analysis required 3 hours, by dividing that same fluid volume into 65 parallel channels using the present disclosure, the analysis time could be reduced to less than 3 minutes. Since any number of microfluidic channels and/or chips may be utilized at once, the present disclosure also provides redundancy and robustness.

As further described herein, illustrative embodiments of the microfluidic device may also include a compositional analysis apparatus that determines compositional characteristics (C1-C4 hydrocarbons, etc.) of the fluid sample volumes within the channels. The compositional analysis apparatus may be, for example, a chromatographic, optical or NMR apparatus. In such embodiments, the microfluidic devices perform an Equation of State ("EOS") analysis of the fluid sample and/or perform a reservoir simulation based upon the phase and compositional characteristic data. These and other advantages of the present disclosure will be apparent to those ordinarily skilled in the art having the benefit of this disclosure.

FIG. 1 illustrates a microfluidic device 100 for performing a PVT analysis of a fluid in accordance with certain illustrative embodiments of the present disclosure. As will be understood by those ordinarily skilled in the art having the benefit of this disclosure, microfluidic cells are typically micro-sized chips that handle the flow of small amounts of fluid through chambers and canals via an intricate valving and pumping system, much like how computer chips handle the flow of electrons through circuits and transistors. The semiconductor material along the chip may be constricted or otherwise manipulated via application of electrical signals to affect pumping or the opening/closing of valves. However, there are a variety of other techniques and materials utilized in the fabrication and design of microfluidic devices, all of which are considered to be within the scope of the present disclosure.

In this illustrative embodiment, microfluidic device 100 includes inlet port 12 for receiving a fluid sample 14. Fluid sample 14 may be any fluid (liquid or gas) or fluid containing a solid substance or material such as, for example, rock formations, slurries, sands, muds, etc. In the illustrative embodiments described herein, however, fluid sample 14 is a multiphase wellbore fluid (comprising oil, gas, water, solids, for example) consisting of a variety of phase characteristics (i.e., liquid, gas and solid phases) and compositional characteristics such as, for example, C1, C2, C3, C4 and higher hydrocarbons, inorganic gases, groupings of such elements, and saline water. Fluid sample 14 may be provided to microfluidic device 100 in a variety of ways including, for example, through a flow pipe or sample cell containing fluid sample 14.

Microfluidic device 100 includes a plurality of microfluidic channels 16a-k in fluid communication with inlet port 14 to receive a volume of the fluid sample 14. Mofluidic channels 16a-k are parallel to one another such that each inlet of channels 16a-k is in fluid communication with inlet port 12 to thereby receive a volume of fluid sample 14. A plurality of valves 18 are positioned throughout microfluidic device 100 to affect movement and isolation of fluid throughout the device, in addition to manipulation of the walls of microfluidic channels 16a-k (to affect volume). Valves 18 include inlet valves 18a and outlet valves 18b which allow the flow of fluid into and out of channels 16a-k, respectively. Although not illustrated for simplicity, microfluidic device 100 may also comprise any number of additional valves, reservoirs, pumps, mixers, etc., necessary to perform device functions, such as volume expansion. For example, semi-permeable membranes may be used to draw specific phases from the fluid sample volume as, for example, gas in a differential liberation PVT experiment. Also, the pressure of the exterior of the chip may be increased or decreased to ease the restrictions on components such as valves or volume constrictions. In certain other illustrative embodiments, microfluidic channels 18 may comprise a number of additional valves positioned there along so that the volume of fluid injected into microfluidic channels 18 may be altered as desired.

As fluid sample 14 flows into inlet port 12, one or more inlet valves 18a are opened while valves 18b remain closed to allow fluid to flow into, and be contained by, microfluidic channels 16a-k. Fluid may be allowed to flow into one, a subset of, or each microfluidic channel 16a-k. In this illustrative embodiment, an NMR apparatus 20 is positioned adjacent to one or more of microfluidic channels 16a-k in order to generate a magnetic field across the sample volume of fluid contained in the channel. As will be understood by those ordinarily skilled in the art having the benefit of this disclosure, NMR apparatus 20 exposes the fluid sample volumes to a magnetic field and resonant frequency pulses to determine the amount of liquid, gas or solid material (i.e., phase characteristics) within the sample volumes at a given pressure and temperature. The operation of NMR is well known in the art and will not be described in detail herein. NMR apparatus 20 then generates a signal corresponding to each phase characteristic measurement along each microfluidic channel 16a-k.

In certain illustrative embodiments, NMR apparatus 20 applies a homogenous magnetic field across one, a subset of, or each microfluidic channel 16a-k. As will be understood by those ordinarily skilled in the art having the benefit of this disclosure, a homogeneous field is essential to spectroscopy measurements and enables better separation of NMR frequency characteristics associated with different fluid molecules. In addition, a homogeneous field produces a narrow line width making the free-induction-decay signal last longer, thereby providing a stronger signal. In yet other embodiments, NMR apparatus 20 applies a gradient magnetic field across one, a subset of, or each microfluidic channel 16a-k. A gradient field is useful for distinguishing fluid molecules based on their corresponding diffusion characteristics.

As also understood by those skilled persons described herein, the phase characteristics of each fluid sample volume will be dependent upon the pressure and temperature applied to each fluid sample volume. Although not shown, in addition to receiver coils, each microfluidic channel 16a-k includes a transmitter coil to transmit the signals to device circuitry 24 (CPU, for example) for further processing. Such coils may be mounted or fabricated on individual microfluidic channels 16a-k, in certain embodiments.

Device circuitry may be located onboard microfluidic device 100 or at some remote location. Device circuitry 24 comprises a signal processor (not shown), communications module (not shown) and other circuitry necessary to achieve the objectives of the present disclosure, as will be understood by those ordinarily skilled in the art having the benefit of this disclosure. In addition, it will also be recognized that the software instructions necessary to carry out the objectives of the present disclosure may be stored within storage located within device circuitry 24 or loaded into that storage from a CD-ROM or other appropriate storage media via wired or wireless methods. Communications link 26 provides a medium of communication between device circuitry 24 and microfluidic device 100. Communications link 26 may be a wired link, such as, for example, a wireline extending down into a wellbore or a fiber optic cable. Alternatively, however, communications link 26 may be a wireless link, such as, for example, acoustic communication, mud-pulse telemetry and like devices. Also, an electromagnetic device of suitable frequency may be utilized for communication.

Device circuitry 24, via its signal processor, controls operation of microfluidic device 100. Although not shown, microfluidic device 100 comprises a transmitter and receiver (transceiver, for example) (not shown) that allows bi-directional communication over communications link 26 in real time. In certain illustrative embodiments, microfluidic device 100 will transmit all or a portion of the characteristic data to device circuitry 24 for further analysis. However, in other embodiments, such analysis is completely handled by microfluidic device 100 and the resulting data is then transmitted to device circuitry 24 for storage or subsequent analysis.

In addition to various phases, each sample fluid volume also comprises a variety of chemical compositions. Such chemical compositions of the fluid sample volumes include, for example, the presence and quantity of specific inorganic gases such as, for example, $CO_2$ and $H_2S$, organic gases such as methane (C1), ethane (C2) and propane (C3) and saline water, in addition to dissolved ions (Ba, Cl, Na, Fe, or Sr, for example) or various other characteristics (p.H., density and specific gravity, viscosity, total dissolved solids, sand content, etc.). Thus, in an alternative embodiment, one or more compositional analysis apparatuses 22 may be positioned adjacent to one or more of microfluidic channels 16a-k to detect such compositional characteristics. Alternatively, compositional analysis apparatus 22 and NMR apparatus 20 may be positioned around the same microfluidic channel 16. Although only 11 microfluidic channels 16a-k are illustrated, there may be hundreds more, for example. Compositional techniques may be applied to the same channel or different channels and statistically recombined. Nevertheless, once the compositional characteristics are detected, compositional analysis apparatus 22 generates a corresponding signal and transmits it to device circuitry 24 for further processing.

In certain illustrative embodiments, each microfluidic channel 16a-k may be specifically optimized to detect different compositional characteristics of the fluid sample volume in parallel. For example, microfluidic channel 16c may be specifically optimized for detection of C1-C5 hydrocarbons, while microfluidic channel 16d is optimized for C4-C8 hydrocarbon detection by compositional analysis apparatus 22. The analyzer is optimized, however, since pressure temperature and volume may play a role in the optimization the channel itself, and its valve or component configuration provides degrees of freedom for optimization with respect to the analyzer.

Compositional analysis apparatus 22 may be, for example, a chromatographic, optical or NMR apparatus. Gas Chromatography coupled with Mass Spectrometry ("GCMS") is one such chromatographic technique which identifies each component in a complex mixture such as oil, and can provide for each the chemical nature, vapor pressure distribution and boiling point. In addition to MS, GCMS, other chromatographic techniques include, for example, size exclusion chromatography, ion chromatography Fourier transform ion cyclotron resonance mass spectrometry or liquid chromatography. Moreover, wet chemistry techniques, including indicator chemistry, can be used to determine composition. Those ordinarily skilled in the art having the benefit of this disclosure realize these and a variety of other such techniques may be utilized with the present disclosure.

Illustrative optical apparatuses include, for example, those utilizing Integrated Computational Elements ("ICE") cores, also known as a Multivariate Optical Elements ("MOE"). As understood in the art, an ICE core is configured to receive an input of electromagnetic radiation from a substance or sample of the substance and produce an output of electromagnetic radiation from a processing element. Fundamentally, an ICE optical apparatus utilizes ICE structures (or cores) to perform calculations, as opposed to the hardwired circuits of conventional electronic processors. When electromagnetic radiation interacts with a substance, unique physical and chemical information about the substance is encoded in the electromagnetic radiation that is reflected from, transmitted through, or radiated from the sample. This information is often referred to as the substance's spectral "fingerprint." The ICE core extracts the spectral fingerprints of multiple characteristics or analytes within a substance and, using regression techniques, directly converts that information into a detectable output regarding the overall properties of a sample.

In addition, other optical apparatuses may utilize, for example, index of refraction, scattering or atomic layer deposition techniques. However, those ordinarily skilled in the art having the benefit of this disclosure realize these and a variety of other such techniques may be utilized with the present disclosure.

There are a variety of other alterations which may be embodied in the compositional apparatuses utilized in the present disclosure. For example, optogalvanic lamps, holocathode lamps, Q-Dots or HT gas lasers may be utilized as the electromagnetic source of the optical apparatus. An ICE core may generate characteristic information to an optical magnetometer acting as a pump or accept characteristic data from a magnetometer acting as a probe. In addition, an ICE core may also be utilized as an optical pump.

As previously described, the fluid sample volumes may be heated or cooled during the PVT analysis. Thus, with reference to FIG. 1, microfluidic device 100 may also comprise one or more devices to heat or cool the fluid sample volumes within microfluidic channels 16a-k. Such devices may include, for example, thermal electric heating/cooling devices (resistive devices, for example), positioned adjacent to or around microfluidic channels 16a-k. In certain embodiments, device circuitry 24 may control operation and monitoring of the temperatures along each microfluidic channel 16a-k.

Figure 2A:
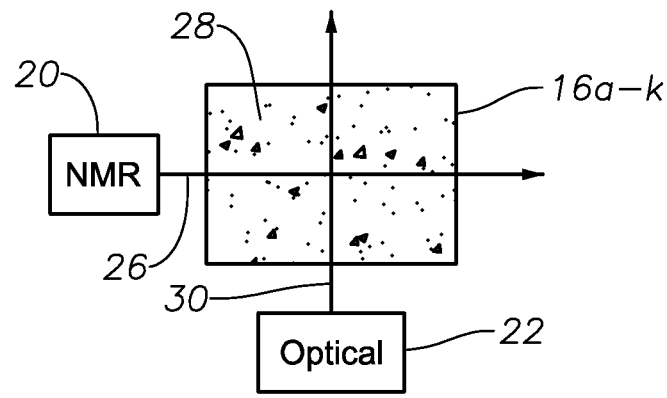
FIGS. 2A and 2B illustrate arrangements for a nuclear magnetic resonance apparatus and a compositional analysis apparatus of the microfluidic device, according to alternative illustrative embodiments of the present disclosure.
Figure 2B:
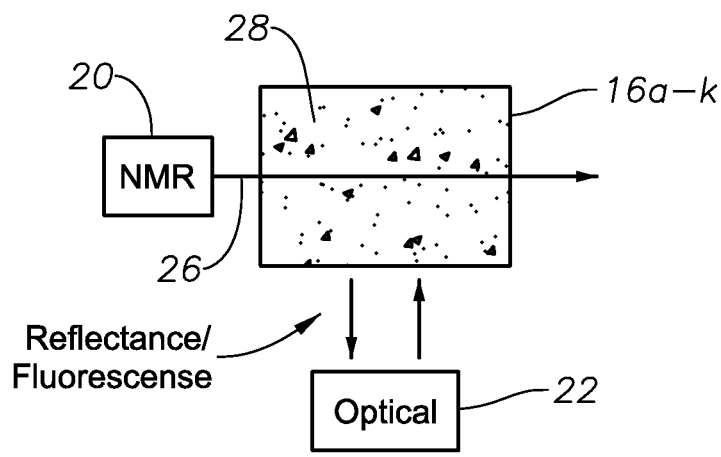

FIG. 2A illustrates a view of microfluidic channel 16a-k taken along line 2A of FIG. 1 to further illustrate certain illustrative embodiments of the present disclosure. Here, NMR apparatus 20 and compositional analysis apparatus 22 (here, an optical apparatus) are positioned along a common microfluidic channel 16a-k in which a fluid sample volume 28 is enclosed. In this embodiment, as illustrated, NMR apparatus 20 generates and emanates magnetic field 26 along an axis perpendicular to an axis in which optical apparatus 22 emanates electromagnetic radiation 30 across fluid sample volume 28. While FIG. 2A reflects a transmission mode design in which the electromagnetic radiation passes through fluid sample volume 28, it is also contemplated herein to reflect electromagnetic radiation off of fluid sample volume 28 using a reflectance or fluorescence mode design as illustrated in FIG. 2B, such as in the case of a fluid sample that is translucent, opaque, or solid. The use of trans-reflectance designs may be especially beneficial in certain embodiments because differential measurement techniques remove the path length dependence of light propagation across microfluidic channels 16a-k. Alternatively, both NMR 20 and optical apparatus 22 may measure the same or substantially the same fluid volume, as illustrated in FIGS. 2A and 2B. FIGS. 2A and 2B are illustrative in nature, as those ordinarily skilled in the art will realize a variety of other optical designs may also be utilized. Note that some optical techniques are more phase sensitive, such as florescent techniques, which are more sensitive for the gas phase. This can isolate, for example, gas composition in a gas/liquid mixture. Absorbance is more sensitive to liquid volumes.

Figure 2C:
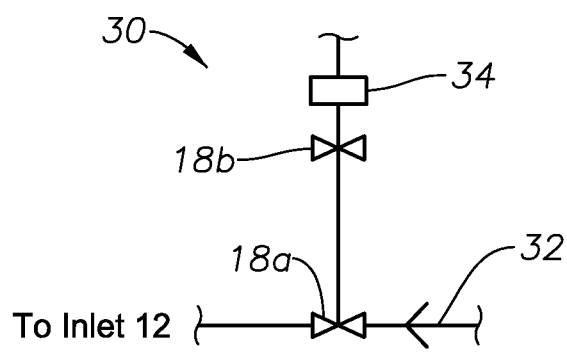
FIG. 2C illustrates a chromatographic column utilized as a microfluidic channel according to an illustrative embodiment of the present disclosure.

As previously described, compositional analysis apparatus 22 may also be a chromatographic apparatus. FIG. 2C illustrates such an illustrative embodiment in which a chromatographic column 30 is utilized as a microfluidic channel 16a-k. As understood in the art, chromatography is a destructive technique; thus, in certain embodiments, the microfluidic channel being utilized for such analysis is solely dedicated to chromatography. Here, chromatographic column 30 comprises an inlet and outlet valve 18a,b as previously described. However, chromatographic column 30 further comprises an inlet 32 for a mobile phase fluid in which to mobilize the fluid sample volume along chromatographic column 30 during testing, as will be understood by those ordinarily skilled persons mentioned herein. Illustrative mobile phase fluids include, for example, hydrogen or helium for gas chromatography, and different organic and inorganic solvents may be utilized for liquid chromatography.

The mobile fluid may be stored in a reservoir located on microfluidic device 100. A detector 34 is also positioned along chromatographic column 30 to detect the compositional characteristics and generate and transmit the corresponding signals to device circuitry 24. Illustrative detectors include, for example, thermal conductivity detectors, MS detectors or optical detectors including index of refraction. During testing, valves 18a,18b may be opened whereby the mobile fluid flows into chromatographic column 30 via inlet 32, thus moving the fluid sample volume up past detector 34 where measurements are taken. Note that the phase specific semi-permeability membrane (e.g., gas phase membrane) can be used to augment analysis of the gas phase in a differential liberation experiment by gas chromatography. If a flash is performed, the entire liquid volume may be analyzed by gas chromatography.

After the phase and compositional characteristic data has been transmitted by NMR apparatus 20 and compositional analysis apparatus 22, respectively, device circuitry 24 may then utilize the data to perform an EOS analysis. In addition, device circuitry 24 may combine the resulting EOS data with fluid viscosity data, rock properties including permeability and porosity and reservoir geometry to conduct a reservoir simulation. There are a variety of software platforms available to conduct such analysis, as will be understood by those ordinarily skilled in the art having the benefit of this disclosure.

Figure 3:
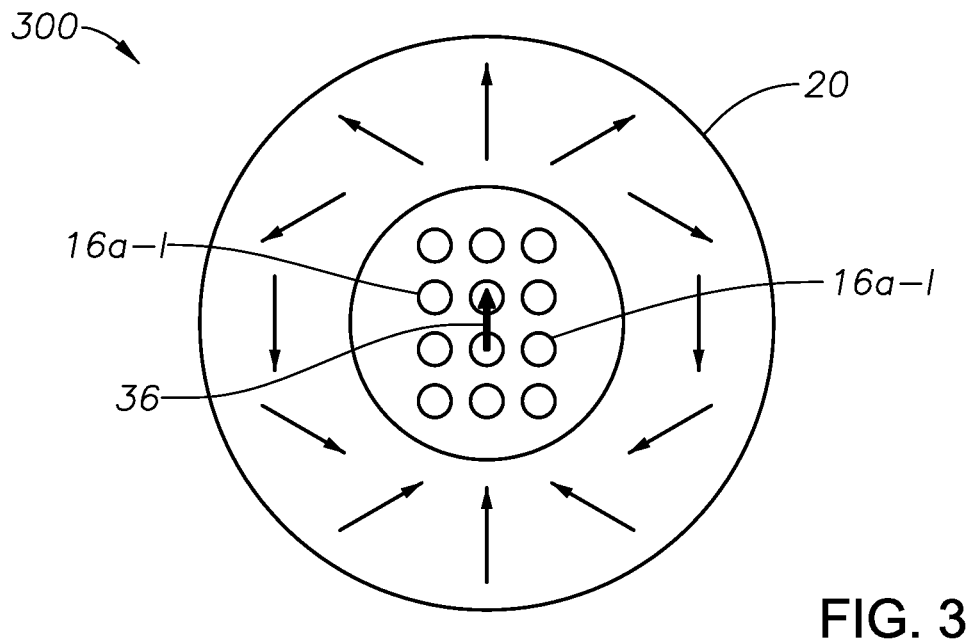
FIGS. 3 and 4 illustrate alternative arrangements for an NMR apparatus utilized within a microfluidic device according to certain illustrative embodiments of the present disclosure.

Now, with reference to FIG. 3, a microfluidic device 300 is illustrated according to an alternate illustrative embodiment of the present disclosure. The fluid inlet/outlets, valves and the parallel arrangement of microfluidic channels 16a-k are the same as those described in FIG. 1. Thus, FIG. 3 is a simplified version of microfluidic device 100 intended to illustrate certain inventive aspects, showing a cut-away topside view similar to that of FIG. 2A. Here, a plurality of microfluidic channels 16a-l is positioned in parallel inside of NMR apparatus 20. NMR apparatus 20 comprises a Halbach cylinder that generates a uniform magnetic field 36 inside the inner hallow space. As will be understood by those skilled persons mentioned herein, a Halbach array is constructed using multiple pieces of magnets in pre-arranged directions such that the magnetic field generated inside the cylinder is highly homogeneous, but the field outside is substantially zero. Each microfluidic channel 16a-l includes an individual transmitter and receiver coil to generate and transmit phase characteristic signals to device circuitry 24. However, alternatively, a single transceiver may also be utilized for performing measurements of all channels.

One advantage of the embodiment of FIG. 3 is that utilization of a single Halbach magnet provides a homogeneous static field for multiple microfluidic channels, which results in a reduction of costs and manufacturability. Another advantage is that the overall size required to implement a plurality of Halbach magnets is very small, thus allowing the microfluidic device to be utilized in very limited spaces.

In yet another illustrative embodiment, multiple parallel microfluidic channels may be mounted on a micro-fabricated chip in a planar configuration. If, for some reason, other electronic circuit or peripheral parts prohibit the use of a reasonable sized Halbach magnet, a unilateral magnetic field configuration may be utilized. There are a variety of magnet designs which can generate a unilateral magnetic field, as will be understood by those ordinarily skilled in the art having the benefit of this disclosure. Moreover, in certain illustrative embodiments described herein, it is not critical that the unilateral magnetic field be spatially homogeneous over a prolonged length of microfluidic channels 16a-k, since each microfluidic channel 16a-k can be tuned to the resonance frequency based upon the strength of the magnetic field at its location.

Figure 4:
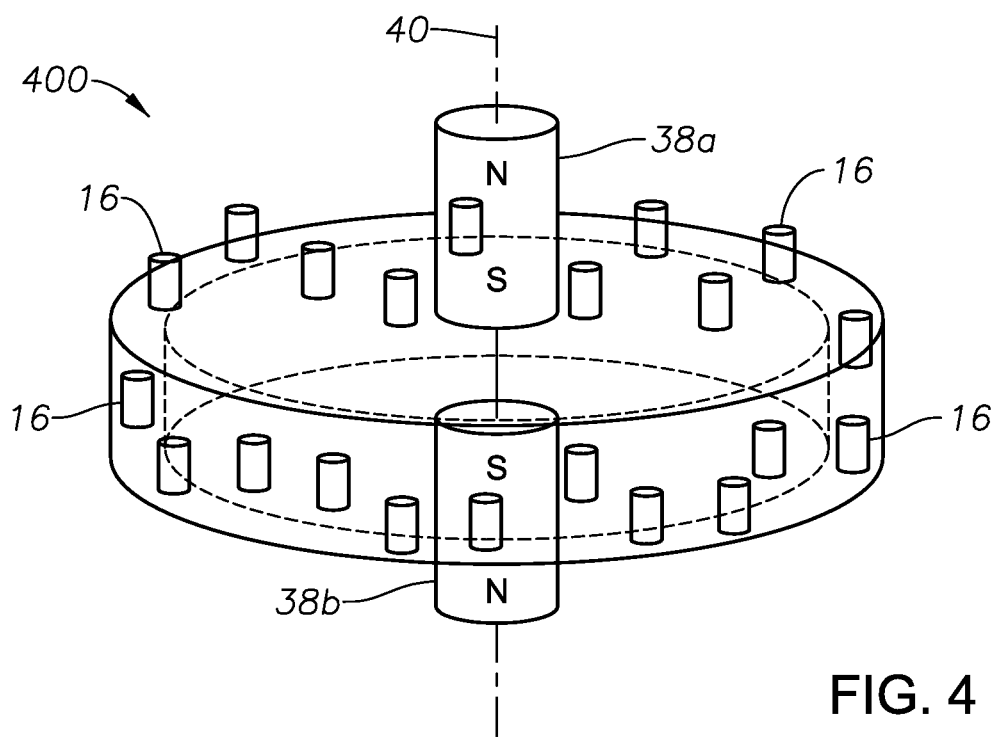

FIG. 4 illustrates a microfluidic device 400 according to yet another alternate illustrative embodiment of the present disclosure. The fluid inlet/outlets, valves and the parallel arrangement of microfluidic channels 16a-k are the same as those described in FIG. 1. Like FIG. 3, FIG. 4 is a simplified illustration of microfluidic device 100 intended to convey certain novel features. NMR apparatus 20 of microfluidic device 400 comprises a first magnet 38a and a second magnet 38b positioned adjacent to one another along a common center axis 40. Although not shown, in certain illustrative embodiments, magnets 38a,b may be held in placed by a mechanical supporting structure positioned between the magnets. Such a supporting structure may be made with, for example, non-magnetic material such that no interference with the field is expected. Alternatively, magnetic material may be used such that the static magnetic field can be enhanced at the sensitive volume. The polarity of magnet 38*a* is opposite the polarity of magnet 38*b* in order to generate a "monopole" magnetic field within the mid-section area surrounding magnets 38*a,b*. Microfluidic channels 16 are arranged in parallel as previously described, and positioned along ring perimeter 42 (which has a relatively uniform magnetic field).

Still referring to FIG. 4, in certain illustrative embodiments, one, a subset of, or all of microfluidic channels 16 are positioned at different vertical and lateral distances from the center axis 40 of first and second magnets 38*a,b* in order to provide measurements of the fluid sample volumes at different magnetic field gradients and strengths. For example, one or more of microfluidic channels 16 may be laterally positioned further from center axis 40 than other microfluidic channels 16. Alternatively, one or more of the channels may be positioned at different vertical positions relative to one another. In such embodiments, when microfluidic channels 16 are filled with the same fluids, measurements at different gradient strengths provide diffusivity measurements, while measurements at different field strengths provide NMR frequency dispersion measurements.

Although not illustrated, microfluidic devices 100, 300, 400 may be deployed downhole utilizing a variety of methodologies such as, for example, in conjunction with MWD or LWD operations. In an illustrative embodiment of the present disclosure, microfluidic devices 100, 300, 400 comprise a part of formation testing tool deployed via a wireline which provides for electrical coupling and bi-directional data communication. The formation testing tool may also include, for example, modules to handle electrical/hydraulic power conversion, fluid sample storage, data recordation, flow control, telemetry, etc., as would be readily understood by persons ordinarily skilled in the art having the benefit of this disclosure. Moreover, microfluidic devices 100,300,400 may further include an on-board CPU to monitor and control operation of microfluidic devices 100,300,400 during PVT analysis operations, or a surface control unit could be utilized to accomplish the same, or some combination of the two.

Figure 5:
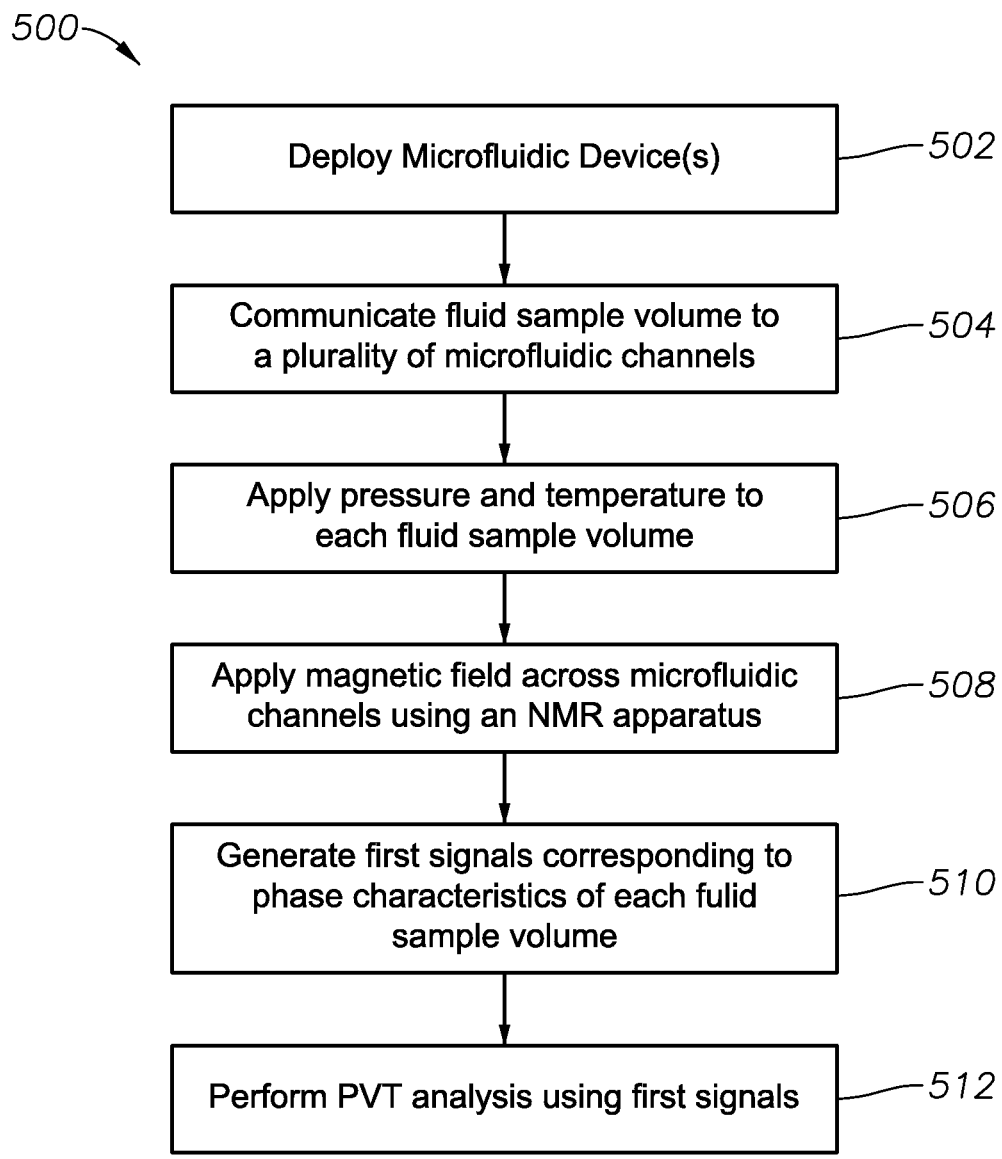
FIGS. 5 and 6 are flow charts of alternate methodologies for performing a PVT analysis, in accordance with certain illustrative methodologies of the present disclosure.

Operation of the present disclosure will now be described with reference to method 500 of FIG. 5. During operation of certain illustrative embodiments of the present disclosure, one or more microfluidic devices 100,300,400 are deployed at block 502 to perform a PVT analysis of wellbore fluid. Such deployment may be, for example, as part of a wireline assembly, logging assembly (logging while drilling or measured while drilling formation test, for example), surface assembly (mud shack, for example), or a drilling assembly (as part of the bit, for example). There would be various methods by which to implement such embodiments, as would be understood by those ordinarily skilled in the art having the benefit of this disclosure. Furthermore, those same skilled persons will realize the microfluidic devices may be deployed downhole as a stand-alone unit or as otherwise desired. Once deployed to the desired position, wellbore fluid is provided to the microfluidic device where it is received by inlet port 12 (FIG. 1). At block 504, fluid sample volumes are then communicated to a plurality of parallel microfluidic channels using various pumps and valves as previously described. For example with reference to FIG. 1, valves 18*a* are opened while valves 18*b* remain closed, thus allowing each microfluidic channel 16*a-k* to fill to any desired volume.

At block 506, a desired pressure and temperature is applied to the fluid sample volumes in each microfluidic channel. As will be understood by those ordinarily skilled in the art having the benefit of this disclosure, the pressure and/or temperature of the microfluidic channels may be applied and/or altered in a variety of ways, including those described herein. Once the pressure and/or temperature of the fluid sample volume is altered, the PVT analysis described herein may be repeated.

At block 508, an NMR apparatus is then utilized to apply a magnetic field across the microfluidic channels. In certain methodologies in which the volume of each fluid sample volume is not known, a one-dimensional NMR profile may be acquired from which the volume can be determined. In other embodiments in which the volume of each fluid sample volume is known, signal amplitude, relaxation and/or diffusion can be monitored to provide fluid discrimination. Additionally, the magnetic field may be generated using a variety of magnetic designs, such as, for example, a single Halbach magnetic cylinder surrounding the microfluidic channels or any of the other designs described herein. Moreover, a homogeneous magnetic field may be applied across one, a subset of, or each microfluidic channel. Alternatively, a gradient magnetic field may be applied across one, a subset of, or each microfluidic channel.

At block 510, utilizing the NMR apparatus, a plurality of first signals corresponding to phase characteristics of each fluid sample volume is generated. In certain illustrative embodiments, the first signals are generated simultaneously, while in others the signals are generated sequentially. This will provide relative or total phase (gas, liquid, solid) volume measurements per microfluidic channel, which will be dependent upon the pressure or temperature applied to it. As previously described, the temperature and/or pressure of the fluid sample volumes may be altered, and the first signals generated again to perform as many PVT experiments as desired. Thus, for example, the same or different pressure, volume or temperature may be applied to the fluid sample volumes as desired.

At block 512, a PVT analysis is then performed based upon the first signals utilizing processing circuitry. Here, in certain embodiments, the phase characteristic data of each channel embodied in the first signals is combined statistically for a complete PVT analysis, thus improving the accuracy over the repeated experiments occurring in the channels. Unlike conventional approaches which utilize a single fluid volume, the present disclosure takes advantage of the parallel channels and small fluid volumes within those channels to rapidly perform multiple PVT experiments simultaneously. For example, the volume and temperature of a channel may be changed over a limited range. Alternatively, different pressure, temperature and volume measurements may be performed in each channel. The different pressure, temperature, and volume measurements are then combined to form an experiment such as, for example, Differential Liberation, Constant Composition, or Constant Volume Depletion. There are also other special PVT analyses including, for example, flow assurance testing, fluid compatibility etc. PVT experiments are performed for the purpose of determining fluid properties (e.g., bulk properties) and fluid behavior (e.g., phase behavior or fluid compatibility).

Thereafter, a statistical average is taken of the resulting phase data to ensure accuracy. One illustrative measurement is the amount of phase at a pressure, volume, temperature point in PVT space with the goal of mapping out the fluid response for the PVT space. For example, in one channel, the gas/liquid split may be determined as 50/50 volume %. In another it might be 49/51, in a third it might be 49/51, in a fourth it might be 48/52. Therefore, according to distribution statistics, the volume split is most likely 49/51. The standard deviation on that measurement is +/−0.8165. Distribution statistics can provide the further statistical description including, for example, confidence of the measurement. Any variety of PVT experiments may be performed utilizing the first signals, such as, for example, phase behavior, transport property or bulk property experiments. As previously mentioned, methodology 500 may be utilized to analyze wellbore fluid. Additionally, in certain methodologies, the PVT analysis is performed while microfluidic device 100,300,400 is downhole.

The illustrative methodologies described herein may be utilized to perform any variety of PVT experiments. For example, substantially identical pressures and temperatures may be applied to two or more fluid sample volumes. Alternatively, different pressures and temperatures may be applied to two or more fluid sample volumes. Accordingly, the present disclosure provides experimental repeatability which greatly reduces the time required for a PVT analysis as compared to conventional approaches. For example, if an experiment was intended to determine the bubble point temperature for reservoir fluid at 3K psi, fifteen microfluidic channels may filled with the same volume of reservoir fluid. Five microfluidic channels are heated to 350 F, five are heated to 360 F, and five are heated to 370 F. The NMR apparatus then generates the phase characteristic signals as described herein, which are ultimately utilized to determine the bubble point temperature for the wellbore fluid at 3K psi. Certain embodiments may also utilize redundant measurements or statistical analysis of the signals to increase accuracy across multiple experiments. Ultimately, any number of microfluidic channels with different pressures, volumes or temperatures may be analyzed for any variety of PVT experiments within or between chips.

Figure 6:
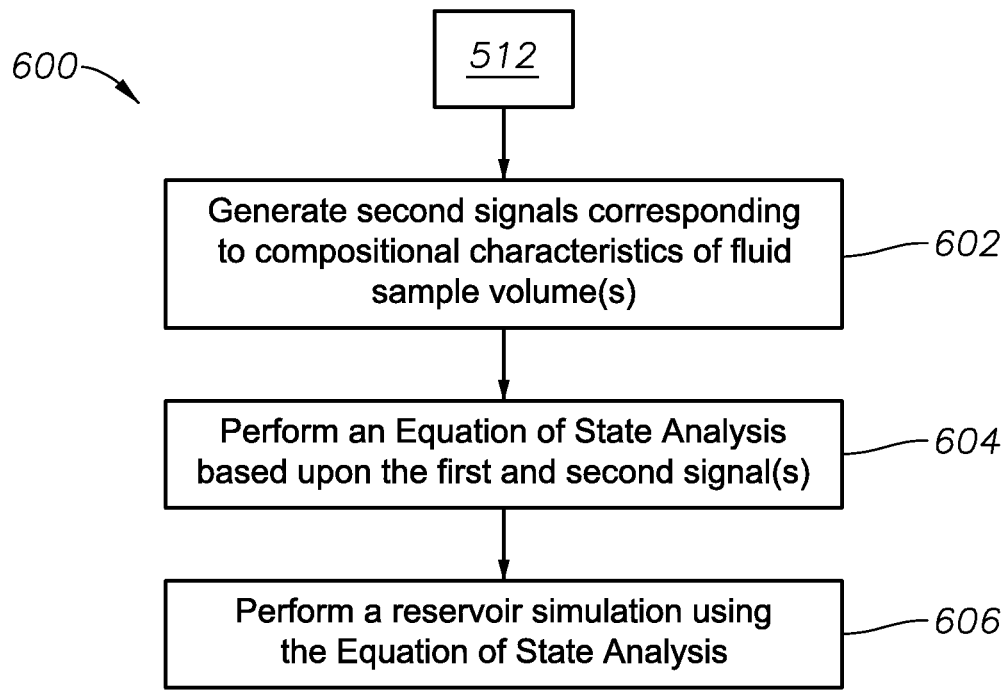

FIG. 6 illustrates another methodology 600 to perform a PVT analysis, in accordance to certain illustrative methods of the present disclosure. At block 602, the microfluidic device 100, 300, 400 generates one or more second signals corresponding to a compositional characteristic of the fluid sample volume utilizing a compositional analysis apparatus (chromatographic, optical or NMR apparatus, for example). Although illustrated as occurring after block 512, block 602 may occur before or concurrent with any of blocks 504-512. In one embodiment, certain microfluidic channels, and their corresponding second signals, correspond to different compositional characteristics of the fluid sample. Nevertheless, at block 604, the first and second signals may be utilized to perform an EOS analysis. At block 606, the equation of state analysis may then be utilized to perform a reservoir simulation of the fluid sample.

Accordingly, illustrative embodiments of the present disclosure described herein make use of microfluidic processes to parallelize the PVT analysis such that part of a pressure, temperature, volume combination is performed separate from others. The PVT data is then recombined statistically for a complete PVT analysis. Utilizing microfluidics as the enabling technology, the present disclosure divides laboratory testing into hundreds, for example, of micro to nano chambers. If, for example, a full PVT analysis would take a week, then by dividing the experiment into 200 parallel microfluidic channels using the present disclosure, the experiment could be completed in less than an hour. Thus, a batch process is parallelized for rapid response via fluidic manipulation, temperature control, pressure control and volume control. Regarding volume, certain embodiments utilize as little as 250 micro-liters or less or 2 milli-liters of fluid with only 8 PVT experimental repeats.

Also, due to the small nature of the microfluidic devices, temperature and pressure control is augmented. In fact, depending on the size of the device, temperature may be rapidly and easily controlled even in a downhole environment utilizing technology such as, for example, thermal electric cooling or thermal electric heating. Combining the technology with optical, or micro-NMR sensing capability including, but not limited to, induction-based or non-induction-based type NMR sensors, then phase behavior and composition may be directly determined in the fluidic chip. Integration of the microfluidic device with chromatographic technology on a micro scale and mass spectrometry completes the capability of a full PVT laboratory.

The size of the microfluidic devices also allows for many statistical repeats of a PVT experiment, or multiple microfluidic station monitoring throughout wireline or LWD sampling operations including, but not limited to, a Pumpout. The size of the microfluidic devices also enables convenient location of devices in, or associated with, sampling chambers or surface transfer apparatuses.

Additionally, as previously described, the PVT analysis performed using the present disclosure may relate to phase behavior, transport properties or bulk properties of the fluid sample volume. Transport properties may include viscosity or thermal conductivity. Parallel multidivisional gradient perturbations (temperature, pressure, electric fields) may be realized. Bulk properties may include phase envelope, compressibility, thermal expansion, density, phase transitions (asphaltenes perception, for example), wax appearance, and analytical properties (pour point, cloud point, metals content, cut densities, cut viscosities, etc.). Other PVT analysis may include special tests such as, for example, differential liberation, constant composition, constant volume depletion, swell tests, fluid compatibility or flow assurance. Other fluids may be injected into the microfluidic channels for mixing with the fluid sample volume to perform fluid compatibility tests. Physical and chemical properties of refinery separations, sulfur content (speciation) and ash content may also be analyzed.

Figure 7A:
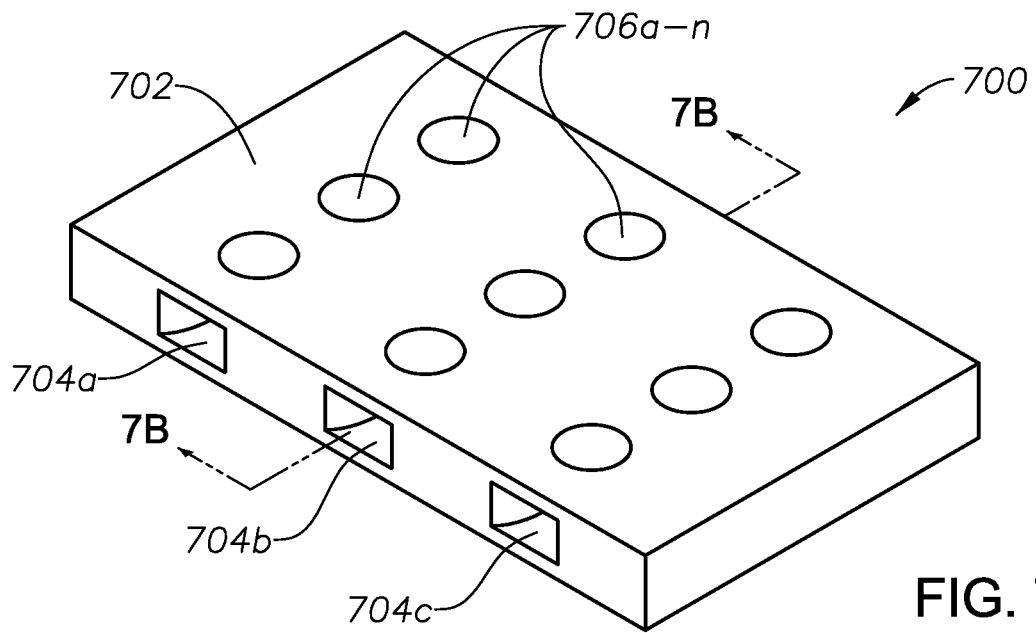
FIG. 7A is a three-dimensional illustration of a more detailed embodiment of a microfluidic optical computing device utilizing a multivariate optical calculation device as the compositional analysis apparatus, according to certain illustrative embodiments of the present disclosure.

FIG. 7A is a three-dimensional illustration of a more detailed embodiment of a microfluidic optical computing device 700 utilizing a multivariate optical calculation device as the compositional analysis apparatus, according to certain illustrative embodiments of the present disclosure. As previously described herein, the multivariate optical calculation device utilizes an ICE core, or MOE, to perform regression calculations to thereby determine compositional characteristics (also referred to herein as "properties") of fluid samples. Microfluidic optical computing device 700 includes a device substrate 702 having matrices of channels 704*a-c* extending there-through in which to receive a fluid sample. Other embodiments may contain more or less channels 704. A plurality of detectors 706*a-n* are positioned along a surface of device substrate 702 such that the axis of each detector 706 transverses its respective channel 704.

Figure 7B:
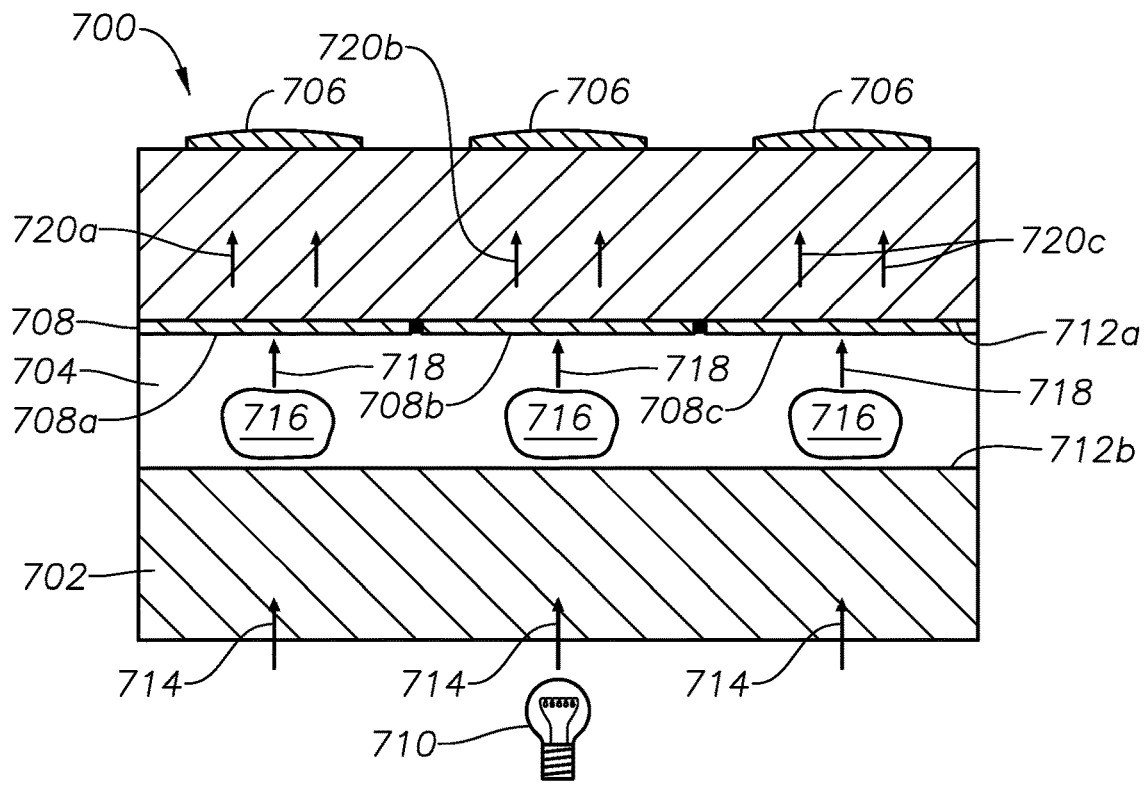
FIGS. 7B-7D is a schematic sectional representation of a microfluidic optical computing device along line 7B of FIG. 7A, according to alternate illustrative embodiments of the present disclosure.

FIG. 7B is a schematic sectional representation of microfluidic optical computing device 700 along line 7B of FIG. 7A, according to one illustrative embodiment of the present disclosure. In this example, microfluidic optical computing device 700 includes a multivariate optical calculation device having one or more light sources 710, an ICE core 708 and detectors 706. The microfluidic optical calculation device is integrated into device substrate 702 to thereby perform a regression calculation on light emanating from a fluid sample to thereby produce a signal that corresponds to one or more properties of the fluid sample. In the embodiment of FIGS. 7A and 7B, ICE core 708 is deposited onto the inside surface of a first side 712a of channel 704. In alternate embodiments, however, ICE core 708 may be deposited on both sides of channel 704 or on a second side 712b of channel 704.

During fabrication, microfluidic optical computing device 700 may be made in two parts which, when assembled, form microfluidic channels 704. As such, the ICE core 708 would be deposited onto one or both sides 712 of channel 704 using a deposition technique. A variety of deposition techniques may be utilized, such as, for example, e-beam or reactive magnetron sputtering, as will be understood by those ordinarily skilled in the art having the benefit of this disclosure. Alternatively, the ICE core may be deposited using Atomic Layer Deposition ("ALD"), which is a chemical vapor deposition technique. Use of ALD would allow microfluidic optical computing device 700 to be formed as one monolithic device. In this example, ICE core 708 may also be deposited by liquid chemical deposition, followed by solvent extraction (evaporation).

Referring to FIG. 7B, ICE core 708 is comprised of multiple ICE cores 708a-c positioned side-by-side in a direction substantially parallel to the axis of channel 704. Alternatively, however, ICE core 708 may comprise only one ICE core. Use of more than one ICE core will allow the measurement of more than one analyte present within the fluid sample flowing through channel 704. Note that manufacturing of this embodiment would require split channel fabrication since masking would be necessary to deposit the multiple ICE cores. As shown, each ICE core 708a-c has its own detector 706a-c to analyze and quantify light emanating from the corresponding ICE core. Thus, the number of detectors 706 is contingent upon the number of ICE cores 708. Detectors 706 may be any device capable of detecting electromagnetic radiation, and may be generally characterized as an optical transducer, as understood in the art. Detectors are further configured to produce an output signal (not shown) in the form of a voltage or current that corresponds to the particular property of the fluid sample. Lastly, one or more broadband electromagnetic radiation sources 710 are positioned opposite detectors 706 to produce light to cover the detector array area.

During operation of microfluidic optical computing device 700, electromagnetic source(s) 710 produce electromagnetic radiation 714 which emanates through the optical transparent device substrate 702 to optically interact with fluid sample 716 flowing through channel 704. After being illuminated with electromagnetic radiation 714, fluid sample 716 containing an analyte of interest (a characteristic/property of the sample, for example) produces an output of electromagnetic radiation (sample-interacted light 718, for example). Sample-interacted light 718 is then directed to ICE cores 708a, b and c, each being designed to approximate or mimic the regression vector of a property within fluid sample 716, to thereby produce corresponding optically-interacted light 720a-c. In this embodiment, optically interacted light 720a-c, which is related to a property of interest, is conveyed to detectors 706 for analysis and quantification. Detectors 706 are further configured to produce an output signal (not shown) in the form of a voltage that corresponds to the particular property or properties of fluid sample 716.

Ultimately, remote processing circuitry (or a processor on-board device 700) analyzes the spectral information of the output signal to determine the property of interest. Although not specifically shown, one or more spectral elements may be employed in microfluidic optical computing device 700 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation.

Figure 7C:
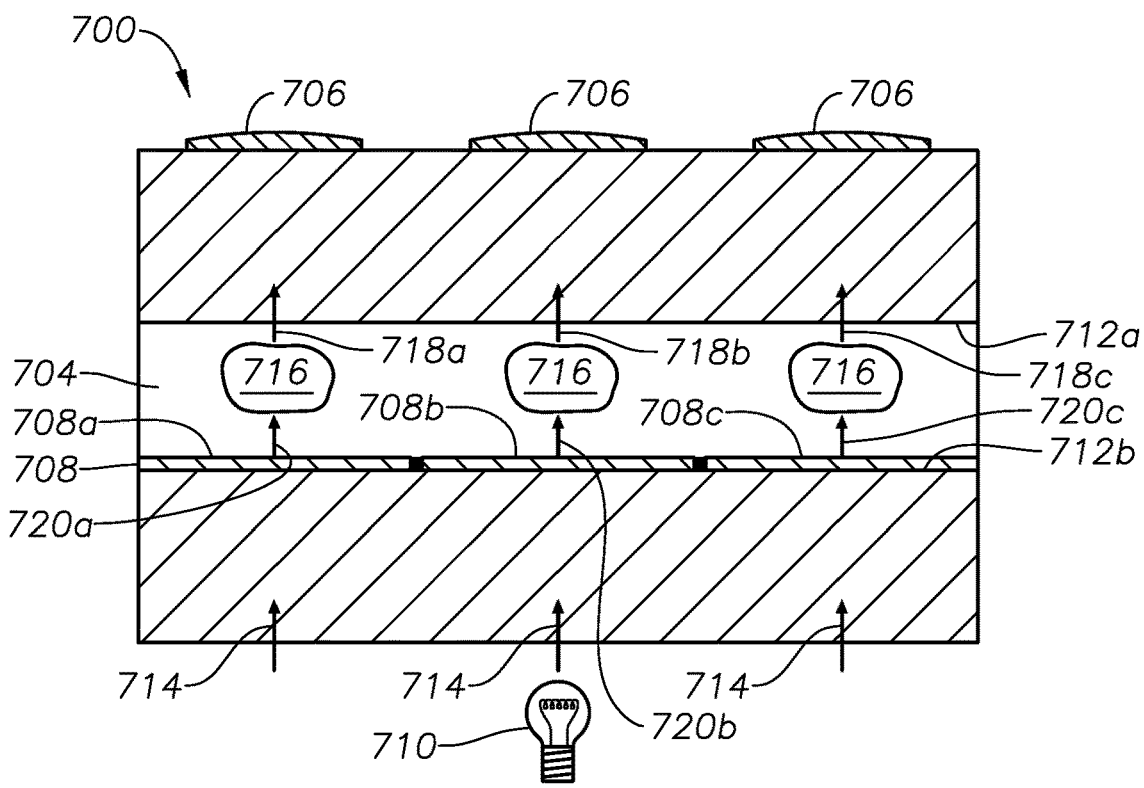

FIG. 7C is a schematic sectional representation of microfluidic optical computing device 700 along line 7B of FIG. 7A, according to an alternative illustrative embodiment of the present disclosure. Microfluidic optical computing device 700 is somewhat similar to the device of FIG. 7B and, therefore, may be best understood with reference thereto, where like numerals indicate like elements. In contrast, however, microfluidic optical computing device 700 of FIG. 7C has ICE cores 708a-c deposited along the inside surface of side 712b. Accordingly, during operation, electromagnetic radiation 714 optically interacts with ICE cores 708a-c to produce optically interacted light 720a-c, whereby ICE cores 708a-c are again configured to be associated with one or more properties of fluid sample 716. Optically-interacted light 720a-c then optically interacts with fluid sample 716 to produce corresponding sample-interacted light 718a-c which, due to its ICE core, has already been filtered to detect the desired property of interest. Detectors 706 then receives sample-interacted light 718a-c and generates the corresponding signals as previously described.

The operation of device 700 of FIG. 7C is somewhat different from that of FIG. 7B in that ICE core 708 is before fluid sample 716. However, those ordinarily skilled in the art having the benefit of this disclosure will readily understand the operation of such an embodiment. As understood by those skilled persons, the dot product the multivariate optical calculation device is cumulative (i.e., A*B=B*A). Thus, the ICE core may be positioned before or after the sample. In those embodiments where the ICE core is before the sample, electromagnetic radiation from the source first interacts with the ICE core (A). The ICE core transforms the source radiation by weighting the intensity of each wavelength by the transmission value of the ICE core at that wavelength. ICE encoded light thereafter interacts with the sample (B), which further modifies the encoded light. Thereafter, the light is integrated at the detector and the property or properties of interest are analyzed and quantified.

Figure 7D:
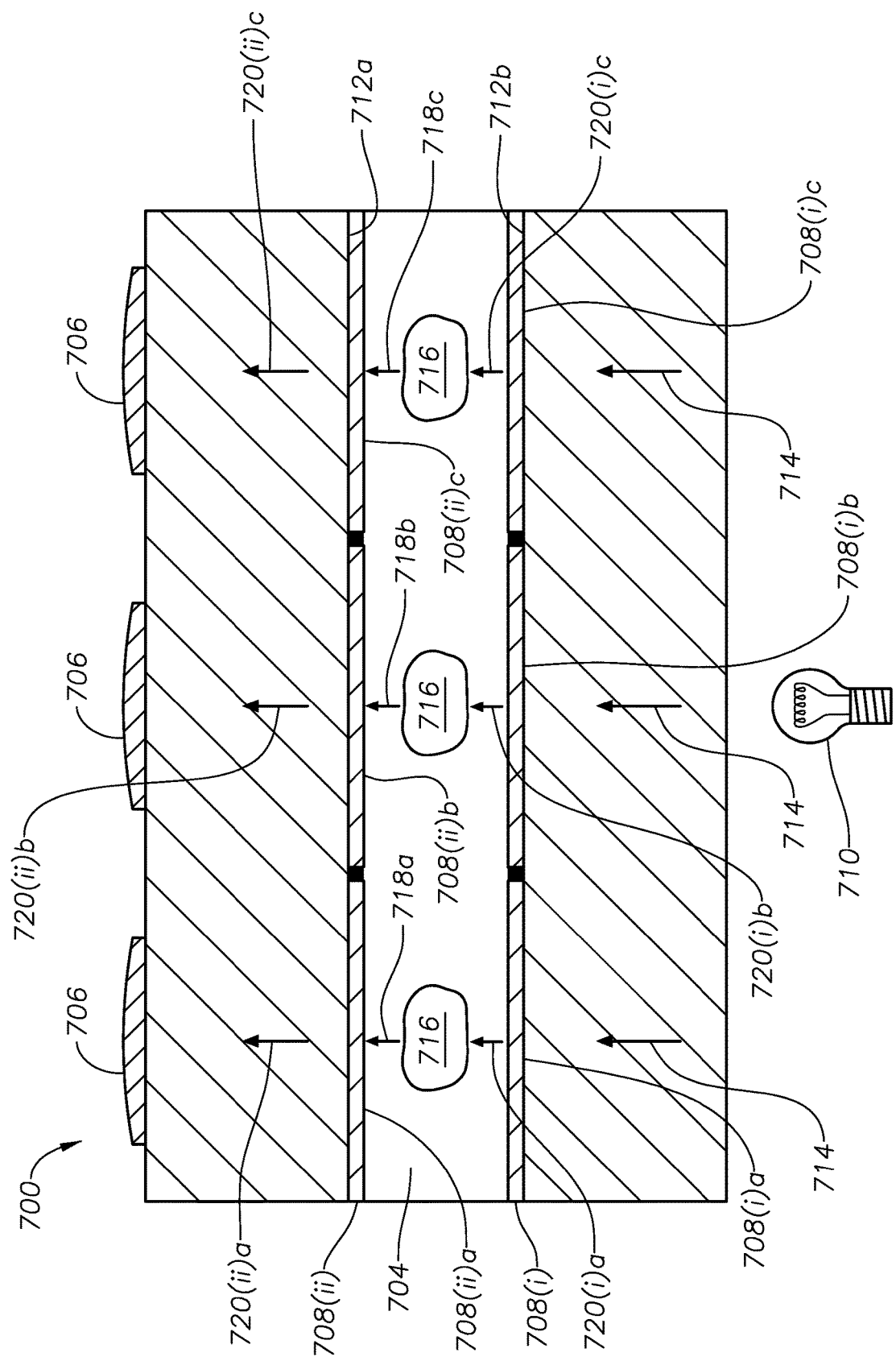

FIG. 7D is a schematic sectional representation of microfluidic optical computing device 700 along line 7B of FIG. 7A, according to yet another alternative illustrative embodiment of the present disclosure. Microfluidic optical computing device 700 is somewhat similar to the device of FIG. 7B and, therefore, may be best understood with reference thereto, where like numerals indicate like elements. In contrast, however, microfluidic optical computing device 700 of FIG. 7D has ICE cores 708a-c deposited along the inside surface of both sides 712a,b. Accordingly, during operation, electromagnetic radiation 714 optically interacts with a first side (i) of ICE core 708, referred to as 708(i), to produce a first optically interacted light 720(i)a-c. First optically interacted light 720(i)a-c then optically interacts with fluid sample 716 to produce sample-interacted light 718a-c, which then optically interacts with a second side (ii) of ICE core 708, referred to as 708(ii), to produce second optically interact light 720(ii)a-c. Detectors 706 then receives second optically interacted light 720(ii)a-c and generates the corresponding signals as previously described.

Still referring to FIG. 7D, first and second sides 708(*i*) and 708(*ii*) have been configured to be associated with one or more properties of the fluid sample. In one illustrative embodiment, the layers forming first and second sides are deposited equally, thus making the first and second sides equivalent. Also, given is the typical ICE equation C=G (A*I)+O, where C is the property of interest, G and O are the gain and offsets of the calibration, respectively, and A and I are the intensities of the sample spectrum and ICE core at each wavelength, respectively. A*I is the dot product, and in this case it would be A*2I, because light goes through the ICE core twice. As a result, we can then solve for C=G (A*2I)+O, or C=2G(A*I)+O.

In those embodiments described herein in which ICE cores are positioned in side-by-side fashion, optical cross-talk may be minimized via a variety of ways. For example, an aperture layer can be added between the substrate and detector to provide a restrictive field of view to prevent cross-talk. Another example would have the thickness of substrate between the fluid channel/ICE side 708(*ii*) and the detector to be sufficiently small to restrict the detectors field of view. Another method to minimize or eliminate cross-talk is to space the ICE core and detector units far enough apart to restrict the detector's field of view. Lastly, combinations of the above methods could be used to minimize the cross-talk while keeping the device small yet accurate Channels 704 may take a variety of shapes. FIGS. 8A-C are cross sectional views of alternative geometries of the fluid channels according to certain illustrative embodiments of the present disclosure. In FIG. 8A, channel 704 is shown having a circular geometry with an ICE core 708 deposited along all sides (as described above in FIG. 7D). The darkened arrow indicates the flow of electromagnetic radiation through the channel. Alternatively, ICE core 708 may only be deposited on one side of channel 704, as described above in FIGS. 7B and 7C. FIG. 8B illustrates a channel 704 having a rectangular geometry with an ICE core 708 deposited on both sides. FIG. 8C shows a channel 704 with a square geometry, also having an ICE core 708 deposited on both sides. As with FIG. 8A, the embodiments of FIGS. 8B and 8C can have ICE cores deposited on only one side, as previously described herein. Channels 704 may take various other geometric shapes as will be understood by those ordinarily skilled in the art having the benefit of this disclosure.

FIG. 9A is a schematic sectional representation of microfluidic optical computing device 900 along line 7B of FIG. 7A, according to one illustrative embodiment of the present disclosure. Microfluidic optical computing device 900 is somewhat similar to the device of FIG. 7B and, therefore, may be best understood with reference thereto, where like numerals indicate like elements. In contrast, however, microfluidic optical computing device 900 of FIG. 9A has an ICE core 902 deposited onto device substrate 702. ICE core 902 may be deposited suing a variety of techniques including, for example, ALD or chemical solvent evaporation (organic layers, for example). As previously described, detectors 706 have been deposited or positioned on top of ICE core 902 using a suitable technique.

As further shown in FIG. 9A, the number of detectors 706 are determined based upon the number of ICE cores 902 which, in this example, include ICE cores 902*a*, *b* and *c*. As such, microfluidic optical calculation device of device 900 is designed to detect three or more properties of fluid sample 716. During operation, electromagnetic radiation 714 is collimated again to optically interact with fluid sample 716 to produce sample-interacted light 718. Sample-interacted light 718 then optically interacts with ICE cores 902*a-c*, which have been designed to approximate or mimic the regression vector of one or more properties property within fluid sample 716, to thereby produce optically-interacted light 720*a-c*. Detectors 706 then receives optically-interacted light 720*a-c* and generates the corresponding signals as previously described.

Figure 9B:
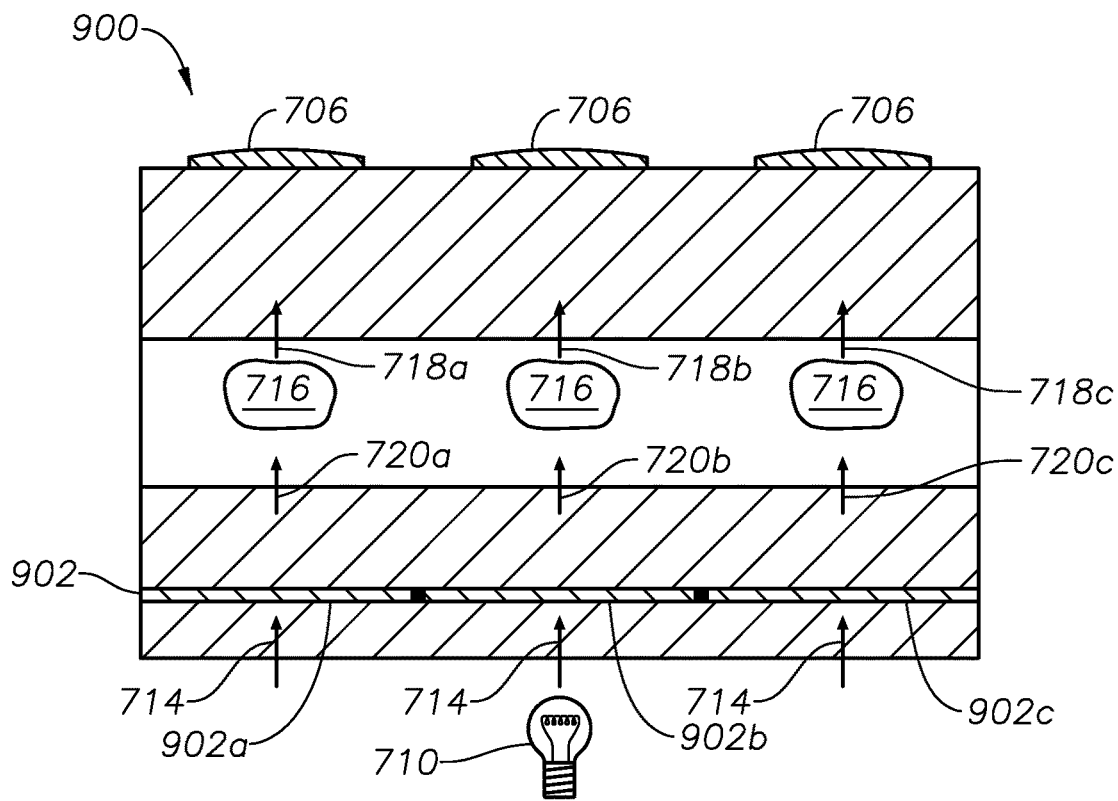

FIG. 9B is a schematic sectional representation of microfluidic optical computing device 900 along line 7B of FIG. 7A, according to one illustrative embodiment of the present disclosure. Microfluidic optical computing device 900 is somewhat similar to the device of FIG. 9A and, therefore, may be best understood with reference thereto, where like numerals indicate like elements. In contrast, however, microfluidic optical computing device 900 of FIG. 9B has an ICE core 902 deposited onto device substrate 702 on the side opposite to that of FIG. 9A. Thus, during operation, electromagnetic radiation 714 optically interacts with ICE cores 902*a-c*, which are configured to be associated with one or more properties of fluid sample 716, to thereby produce optically-interacted light 720*a-c*. Optically-interacted light 720*a-c* optically-interacts with fluid sample 716 to further modify the encoded light and produce sample-interacted light 718*a-c*. Detectors 706 then receives sample-interacted light 718*a-c* and generates the corresponding signals as previously described.

Figure 10:
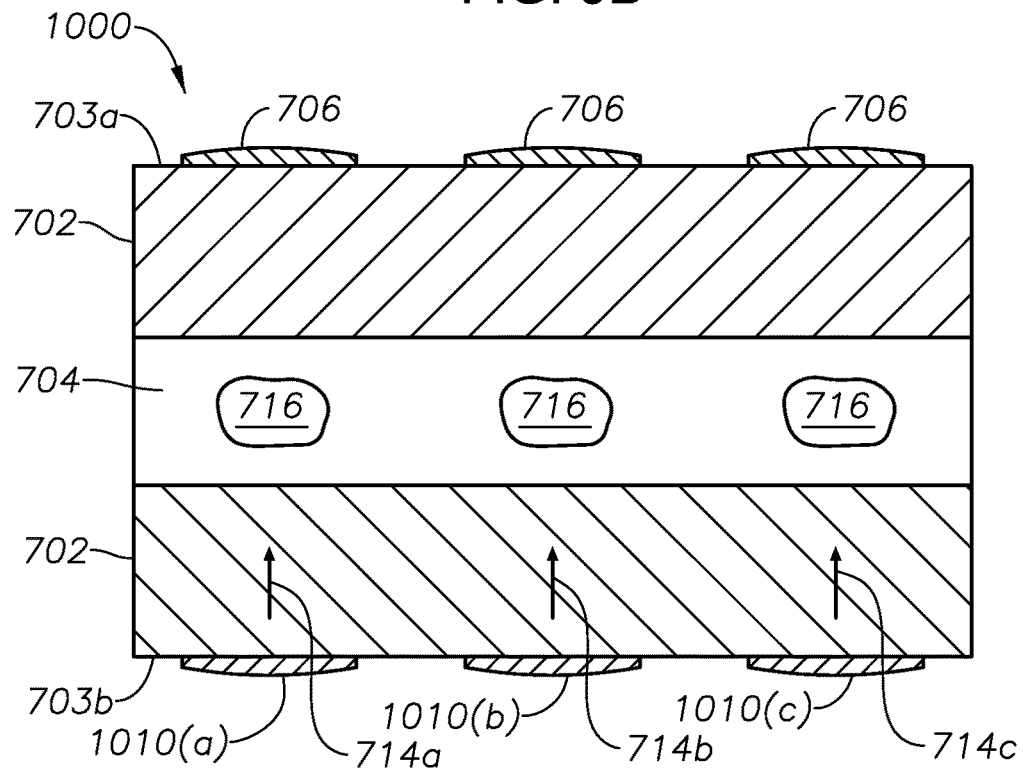
FIG. 10 is a schematic sectional representation of microfluidic optical computing device along line 7B of FIG. 7A having radiation sources deposited on the device substrate, according to one illustrative embodiment of the present disclosure.

FIG. 10 is a schematic sectional representation of microfluidic optical computing device 1000 along line 7B of FIG. 7A, according to one illustrative embodiment of the present disclosure. Microfluidic optical computing device 900 is somewhat similar to the foregoing devices described herein and, therefore, may be best understood with reference thereto, where like numerals indicate like elements. In contrast, however, microfluidic optical computing device 1000 includes electromagnetic radiation sources 1010*a-c* that are each individually deposited directly onto the surface of device substrate 702 by suitable techniques. The ICE core(s) may be positioned as described in any other embodiments mentioned herein.

As shown in FIG. 10, electromagnetic radiation sources 1010*a-c* have been deposited on an exterior surface 703*b* opposite a surface 703*a* on which detectors 706 have been deposited. As previously described, channel 704 extends through substrate 702 in a direction substantially parallel to surfaces 703*a,b*. In one embodiment, electromagnetic radiation sources 1010*a-c* are an array of light sources each with a broad wavelength output, or individually with different wavelength bands that approximate a broader band of excitation when summed, or as viewed by their corresponding detectors 706. The electromagnetic radiation source array can be designed to be spatially tuned to provide the needed wavelength band required by ICE core(s). The array of electromagnetic radiation sources 1010*a-c* illuminates fluid sample 716 in channel 704 with a wavelength band as a function of area. If electromagnetic radiation sources 1010*a-c* are of the same wavelength band, then the illumination is equivalent to a single light source. Conversely, an array of different light sources can provide reliability by incorporating redundant light sources. In other embodiments, electromagnetic radiation sources 1010 with smaller wavelength bands can be coupled to form a larger wavelength band in an area of channel 704, and thus the area around individual ICE cores and detectors. The arrangement of an array of electromagnetic radiation sources 1010 can provide an increase in signal-to-noise rat("SNR") compared to a single lamp with collimating optics. Accordingly, smaller microfluidic devices can be achieved by incorporation of the light source onto the device.

Figure 11:
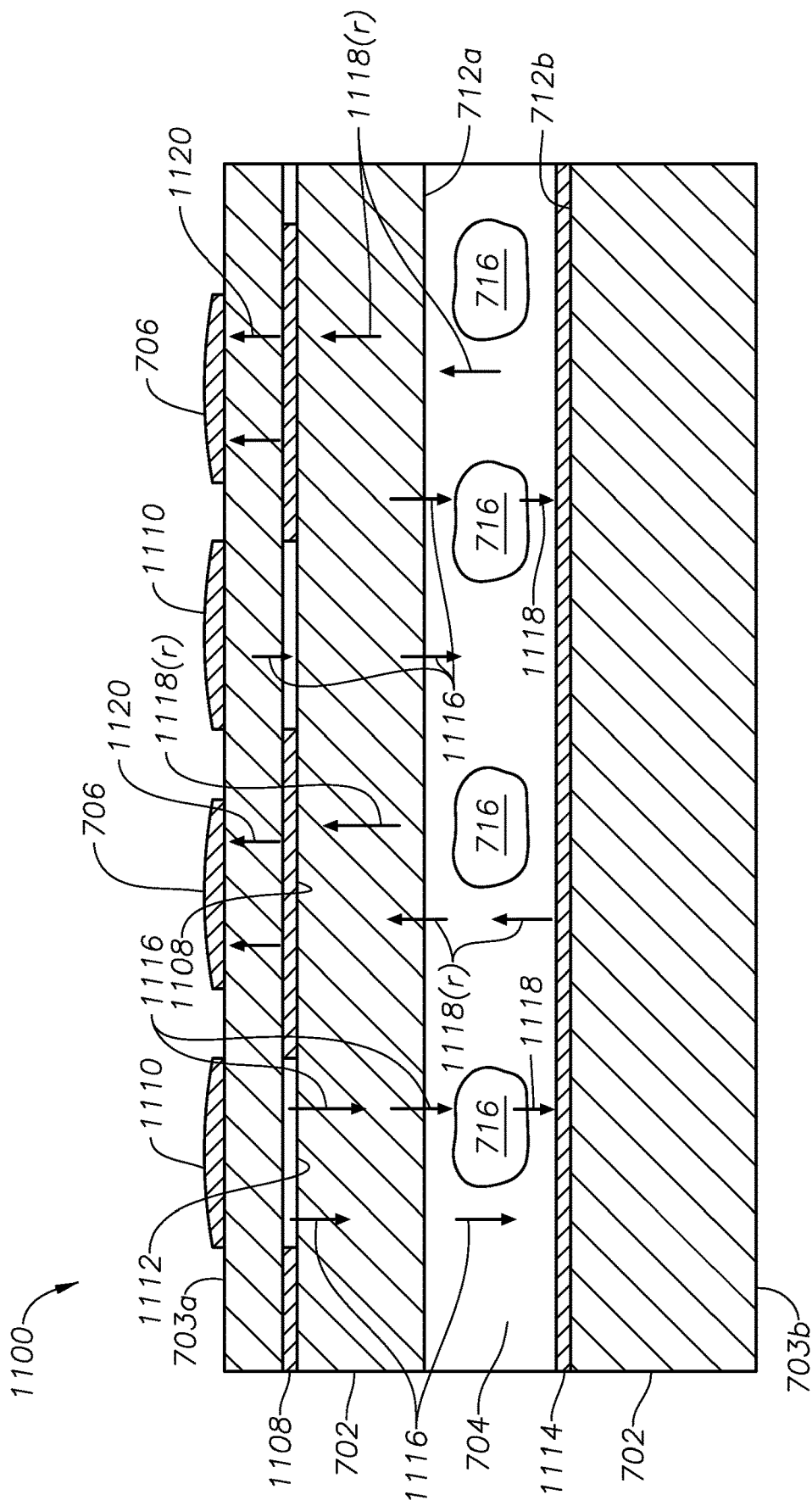
FIG. 11 is a schematic sectional representation of microfluidic optical computing device having an array of radiation sources and detectors along the same surface of the device substrate, according to an alternative illustrative embodiment of the present disclosure.

FIG. 11 is a schematic sectional representation of microfluidic optical computing device 1100, according to an alternative illustrative embodiment of the present disclosure. Microfluidic optical computing device 1100 is somewhat similar to the device of FIG. 10 and, therefore, may be best understood with reference thereto, where like numerals indicate like elements. In contrast, however, microfluidic optical computing device 1100 includes an array of electromagnetic radiation sources 1110 and detectors 706 along first surface 703a, which operate in reflection mode. In FIG. 11, there are two electromagnetic radiation sources 1110 and two detectors 706 which have been deposited side-by-side along, in alternating fashion, along first surface 703a. This arrangement of detectors 706 and electromagnetic radiation sources 1110 allows for one or more analytes of interest to be measured within fluid sample 716.

ICE cores 1108 (three are shown in this example) have also been deposited in side-by-side fashion along device substrate 702 as in previous embodiments, except in device 1100, ICE cores 1108 include void regions 1112 between each. ICE cores 1108 can be deposited before the detector-source layer, or deposited inside the first layer of the channel 704. Void regions 1112 are positioned adjacent to electromagnetic radiation sources 1110, while ICE cores 1108 are positioned adjacent to detectors 706. A reflector 1114 is positioned along second side 712b of channel 704, which is opposite of surface 703a, in order to perform the reflection, as described below.

During operation of microfluidic optical computing device 1100, electromagnetic radiation 1116 passes through void regions 1112 between ICE cores 1108 to optically interact with fluid sample 716 passing through channel 704 to produce sample-interacted light 1118. The electromagnetic radiation 1116 passing through the void regions essentially acts like a lamp that illuminates a room (i.e., the entire channel 704). Sample-interacted light 1118 is then encounters reflector 1114, where it is reflected back to ICE cores 1108 as 1118(r), and further modified by ICE cores 1108 to produce optically-interacted light 1120, whose intensity is directly proportional to the property measured by ICE cores 1108. Detectors 706, which are aligned with one ICE core 1108 each, then receives optically-interacted light 1120 and generates the corresponding signals as previously described. In certain illustrative embodiments, electromagnetic radiation sources 1110 and detectors 706 may be strategically arranged to provide flexibility of allowing multiple different lamp-ICE core combinations on a single chip.

Although not shown, device circuitry on-board microfluidic optical computing devices 700, 900, 1000 or 1100, or remote thereto, analyzes the signal(s) to determine the one or more properties of fluid sample 716. Moreover, the illustrative embodiments described herein may be embodied in modules or other housings and deployed in downhole or completion applications such as, for example, along a pipeline or wellbore. In addition to PVT and other applications described herein, the illustrative microfluidic optical computing devices may be utilized in a variety of others environments. Such environments may include, for example, those as diverse as those associated with surface and undersea monitoring, satellite or drone surveillance, pipeline monitoring, or even sensors transiting a body cavity such as a digestive tract. Within those environments, the optical computing devices may be utilized to detect sample properties/characteristics in real-time.

Figure 12A:
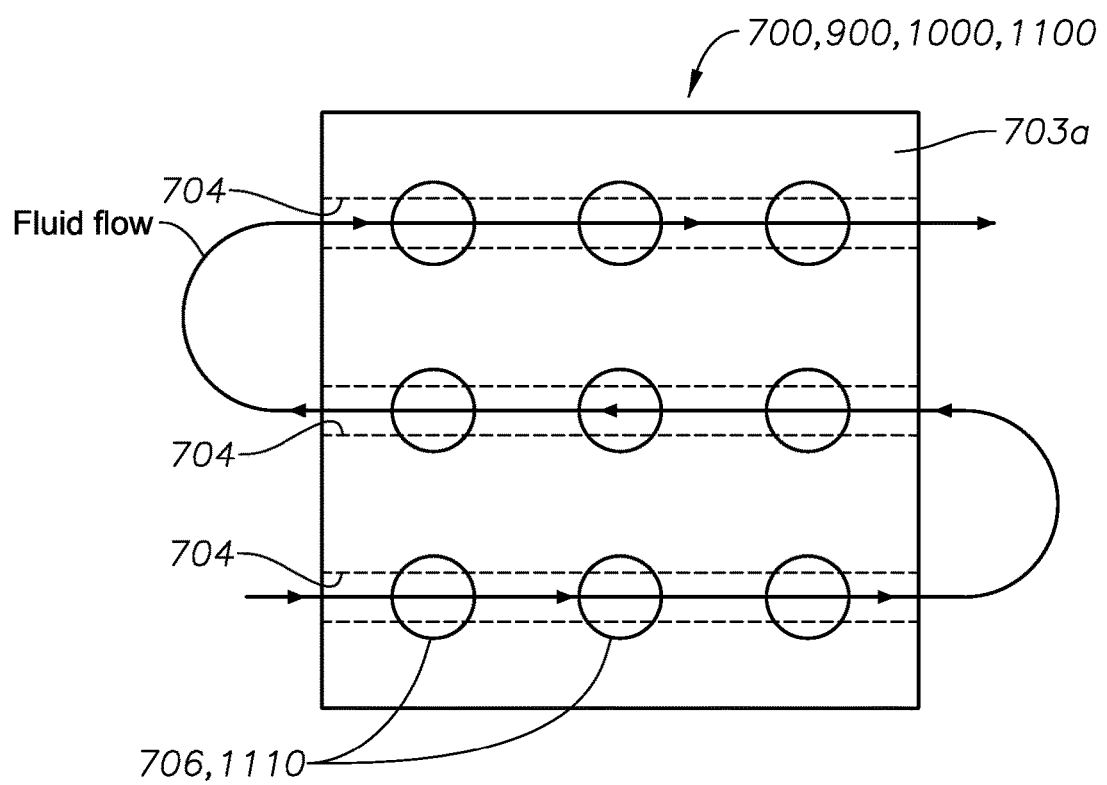
FIGS. 12A and 12B are alternative arrangements for the flow of a fluid sample through various illustrative microfluidic optical computing devices.
Figure 12B:
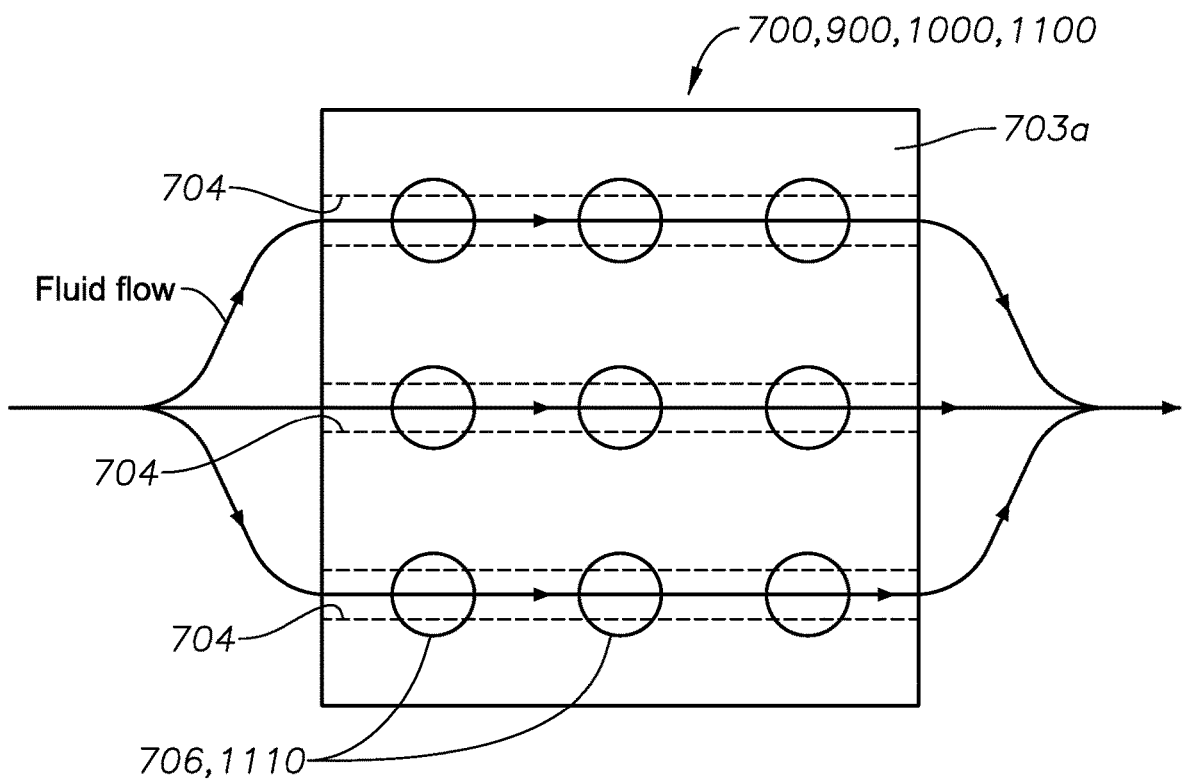

FIGS. 12A and 12B are alternative arrangements for the flow of fluid sample 716 through microfluidic optical computing devices 700, 900, 1000 or 1100. Surface 703a is shown having a plurality of detectors 706 and/or radiation sources 1110 deposited thereon (in a left-to-right orientation that tracks channels 704), as described in one or more of the illustrative embodiments described above. In a first example of FIG. 12A, the flow of fluid sample 716 may be circulated through each channel 704 is a sequential fashion, while FIG. 12B shows fluid sample 716 being diverted in parallelized fashion. Those ordinarily skilled in the art having the benefit of this disclosure will understand there are a variety of ways in which to provide fluid sample 716 to microfluidic optical computing devices 700, 900, 1000 or 1100.

Accordingly, the microfluidic devices of the present disclosure provide a number of advantages. First, for example, conventional laboratory analysis may be enhanced due to the rapid nature and lower sample requirements of the present disclosure. Second, the microfluidic devices of the present disclosure are easily adaptable between well site and laboratory settings. Third, the present disclosure provides efficient automation in a laboratory, process control, well site or subsea environment. For example, to control a process, measurements are often made to ensure the process is under control. Adjustments to the process may be controlled by a feedback loop automatically with computer algorithms providing the control based on these measurements. Fourth, full rapid chemical analysis in a formation testing environment is provided by the present disclosure.

Embodiments described herein further relate to any one or more of the following paragraphs:

1. A microfluidic optical computing device, comprising a device substrate having a channel therein to receive a fluid sample; and a multivariate optical calculation device positioned to perform a regression calculation on light emanating from the fluid sample within the channel to thereby produce a signal which corresponds to at least one property of the fluid sample, wherein the multivariate optical calculation device is integrated into the device substrate.

2. A microfluidic optical computing device as defined in paragraph 1, wherein the multivariate optical calculation device comprises an Integrated Computational Element ("ICE") core positioned along one side of the channel.

3. A microfluidic optical computing device as defined in any of paragraphs 1-2, wherein the multivariate optical calculation device further comprises an electromagnetic radiation source positioned to produce electromagnetic light which optically interacts with the fluid sample within the channel to produce sample-interacted light, wherein the ICE core is positioned to optically interact with the sample-interacted light to produce optically-interacted light, the ICE core being configured to be associated with the at least one property of the fluid sample within the channel; and a detector positioned to receive the optically-interacted light and thereby generate the signal corresponding to the at least one property of the fluid sample.

4. A microfluidic optical computing device as defined in any of paragraphs 1-3, wherein the multivariate optical calculation device further comprises an electromagnetic radiation source positioned to produce electromagnetic light which optically interacts with the ICE core to produce optically-interacted light, the ICE core being configured to be associated with the at least one property of the fluid sample within the channel, wherein the optically-interacted light optically interacts with the fluid sample to produce sample-interacted light; and a detector positioned to receive the sample-interacted light and thereby generate the signal corresponding to the at least one property of the fluid sample.

5. A microfluidic optical computing device as defined in any of paragraphs 1-4, wherein the multivariate optical calculation device comprises an Integrated Computational Element ("ICE") core positioned along all sides of the channel.

6. A microfluidic optical computing device as defined in any of paragraphs 1-5, wherein the multivariate optical calculation device further comprises an electromagnetic radiation source positioned to produce electromagnetic light which optically interacts with a first side of the ICE core, then optically interacts with the fluid sample within the channel, then optically interacts with a second side of the ICE core positioned opposite the first side to thereby produce optically-interacted light, the ICE core being configured to be associated with the at least one property of the fluid sample within the channel; and a detector positioned to receive the optically-interacted light and thereby generate the signal corresponding to the at least one property of the fluid sample.

7. A microfluidic optical computing device as defined in any of paragraphs 1-6, wherein the multivariate optical calculation device comprises an Integrated Computational Element ("ICE") core positioned on the device substrate; an electromagnetic radiation source positioned to produce electromagnetic light which optically interacts with the fluid sample within the channel to produce sample-interacted light, wherein the ICE core is positioned to optically interact with the sample-interacted light to produce optically-interacted light, the ICE core being configured to be associated with the at least one property of the fluid sample within the channel; and a detector positioned to receive the optically-interacted light and thereby generate the signal corresponding to the at least one property of the fluid sample.

8. A microfluidic optical computing device as defined in any of paragraphs 1-7, wherein the multivariate optical calculation device further comprises an Integrated Computational Element ("ICE") core positioned on the device substrate; an electromagnetic radiation source positioned to produce electromagnetic light which optically interacts with the ICE core to produce optically-interacted light, the ICE core being configured to be associated with the at least one property of the fluid sample within the channel, wherein the optically-interacted light optically interacts with the fluid sample to produce sample-interacted light; and a detector positioned to receive the sample-interacted light and thereby generate the signal corresponding to the at least one property of the fluid sample.

9. A microfluidic optical computing device as defined in any of paragraphs 1-8, wherein the multivariate optical calculation device further comprises an Integrated Computational Element ("ICE") core positioned to perform the regression calculation, wherein the device substrate comprises a first exterior surface and a second exterior surface opposite the first exterior surface, the channel extending through the device substrate in a direction substantially parallel to the first and second exterior surfaces; an electromagnetic radiation source positioned to produce electromagnetic light, the electromagnetic radiation source being positioned along the first exterior surface; and a detector positioned to receive an input light and thereby generate the signal corresponding to the at least one property of the fluid sample, the detector being positioned along the second exterior surface.

10. A microfluidic optical computing device as defined in any of paragraphs 1-9, wherein the ICE core comprises a plurality of ICE cores positioned side-by-side along a direction substantially parallel to a direction of the channel; and the detector comprises a plurality of detectors that each correspond to one of the ICE cores.

11. A microfluidic optical computing device as defined in any of paragraphs 1-10, wherein the electromagnetic radiation source comprises a plurality of electromagnetic radiation sources that each correspond to one of the detectors.

12. A microfluidic optical computing device as defined in any of paragraphs 1-11, wherein the device substrate comprises a first exterior surface and a second exterior surface opposite the first exterior surface; the channel extends through the device substrate in a direction substantially parallel to the first and second exterior surfaces; the electromagnetic radiation source is positioned along the second exterior surface, the electromagnetic radiation source comprising a plurality of electromagnetic radiation sources; the detector is positioned along the second exterior surface, the detector comprising a plurality of detectors; the electromagnetic radiation sources and the detectors being positioned side-by-side in an alternating fashion; the multivariate optical computing device further comprising an Integrated Computational Element ("ICE") core positioned on the device substrate, the ICE core comprising a plurality of ICE cores positioned side-by-side such that a void region is positioned between two ICE cores; the channel comprises a reflector positioned along a side of the channel that is opposite the second exterior surface; the electromagnetic radiation sources are positioned adjacent the void regions such that the electromagnetic radiation passes through the void regions to optically interact with the fluid sample, the reflector reflecting the sample-interacted light back toward the ICE cores; and each detector is substantially aligned with one of the ICE cores to receive the optically-interacted light.

13. A microfluidic optical computing device as defined in any of paragraphs 1-12, further comprising a matrix of channels within the device substrate.

14. A microfluidic optical computing device as defined in any of paragraphs 1-13, further comprising a signal processor communicably coupled to the multivariate optical calculation device to determine the at least one property of the fluid sample.

15. A microfluidic optical computing device as defined in any of paragraphs 1-14, wherein the microfluidic optical computing device is positioned along a pipeline or wellbore.

16. An optical computing method utilizing a microfluidic optical computing device as described in any of paragraphs 1-14.

17. An optical computing method as defined in paragraph 16, further comprising deploying the microfluidic optical computing device into a wellbore or pipeline.

18. An optical computing method as defined in any of paragraphs 16-17, further comprising performing a pressure-volume-temperature analysis based upon the signal.

19. An optical computing device, comprising a device substrate having a matrix of channels therein to receive a fluid samples; and a multivariate optical calculation device positioned to perform a regression calculation on light emanating from the fluid samples within the channels to thereby produce signals which correspond to at least one property of the fluid samples, wherein the multivariate optical calculation device is integrated into the device substrate.

20. An optical computing device as defined in paragraph 19, wherein the device is microfluidic; and a plurality of Integrated Computational Element ("ICE") cores are positioned on the device substrate in order to perform the regression calculation.

Although various embodiments and methodologies have been shown and described, the disclosure is not limited to such embodiments and methodologies and will be understood to include all modifications and variations as would be apparent to one skilled in the art. For example, it is not necessary that the computing device be microfluidic, as other embodiments of the present disclosure may be embodied in non-microfluidic systems. Moreover, one or more features of the embodiments described herein may be combined as desired. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. A microfluidic optical computing device, comprising:
    a device substrate having a channel therein to receive a fluid sample; and
    a multivariate optical calculation device positioned to perform a regression calculation on light emanating from the fluid sample within the channel to thereby produce a signal which corresponds to at least one property of the fluid sample, wherein the multivariate optical calculation device is integrated into the device substrate.

2. A microfluidic optical computing device as defined in claim 1, wherein the multivariate optical calculation device comprises an Integrated Computational Element ("ICE") core positioned along one side of the channel.

3. A microfluidic optical computing device as defined in claim 2, wherein the multivariate optical calculation device further comprises:
    an electromagnetic radiation source positioned to produce electromagnetic light which optically interacts with the fluid sample within the channel to produce sample-interacted light,
    wherein the ICE core is positioned to optically interact with the sample-interacted light to produce optically-interacted light, the ICE core being configured to be associated with the at least one property of the fluid sample within the channel; and
    a detector positioned to receive the optically-interacted light and thereby generate the signal corresponding to the at least one property of the fluid sample.

4. A microfluidic optical computing device as defined in claim 2, wherein the multivariate optical calculation device further comprises:
    an electromagnetic radiation source positioned to produce electromagnetic light which optically interacts with the ICE core to produce optically-interacted light, the ICE core being configured to be associated with the at least one property of the fluid sample within the channel,
    wherein the optically-interacted light optically interacts with the fluid sample to produce sample-interacted light; and
    a detector positioned to receive the sample-interacted light and thereby generate the signal corresponding to the at least one property of the fluid sample.

5. A microfluidic optical computing device as defined in claim 1, wherein the multivariate optical calculation device comprises an Integrated Computational Element ("ICE") core positioned along all sides of the channel.

6. A microfluidic optical computing device as defined in claim 5, wherein the multivariate optical calculation device further comprises:
    an electromagnetic radiation source positioned to produce electromagnetic light which optically interacts with a first side of the ICE core, then optically interacts with the fluid sample within the channel, then optically interacts with a second side of the ICE core positioned opposite the first side to thereby produce optically-interacted light, the ICE core being configured to be associated with the at least one property of the fluid sample within the channel; and
    a detector positioned to receive the optically-interacted light and thereby generate the signal corresponding to the at least one property of the fluid sample.

7. A microfluidic optical computing device as defined in claim 1, wherein the multivariate optical calculation device comprises:
    an Integrated Computational Element ("ICE") core positioned on the device substrate;
    an electromagnetic radiation source positioned to produce electromagnetic light which optically interacts with the fluid sample within the channel to produce sample-interacted light,
    wherein the ICE core is positioned to optically interact with the sample-interacted light to produce optically-interacted light, the ICE core being configured to be associated with the at least one property of the fluid sample within the channel; and
    a detector positioned to receive the optically-interacted light and thereby generate the signal corresponding to the at least one property of the fluid sample.

8. A microfluidic optical computing device as defined in claim 1, wherein the multivariate optical calculation device further comprises:
    an Integrated Computational Element ("ICE") core positioned on the device substrate;
    an electromagnetic radiation source positioned to produce electromagnetic light which optically interacts with the ICE core to produce optically-interacted light, the ICE core being configured to be associated with the at least one property of the fluid sample within the channel,
    wherein the optically-interacted light optically interacts with the fluid sample to produce sample-interacted light; and
    a detector positioned to receive the sample-interacted light and thereby generate the signal corresponding to the at least one property of the fluid sample.

9. A microfluidic optical computing device as defined in claim 1, wherein the multivariate optical calculation device further comprises:
    an Integrated Computational Element ("ICE") core positioned to perform the regression calculation,
    wherein the device substrate comprises a first exterior surface and a second exterior surface opposite the first exterior surface, the channel extending through the device substrate in a direction substantially parallel to the first and second exterior surfaces;
    an electromagnetic radiation source positioned to produce electromagnetic light, the electromagnetic radiation source being positioned along the first exterior surface; and
    a detector positioned to receive an input light and thereby generate the signal corresponding to the at least one property of the fluid sample, the detector being positioned along the second exterior surface.

10. A microfluidic optical computing device as defined in any of claims 3, 4 and 6-9, wherein:
the ICE core comprises a plurality of ICE cores positioned side-by-side along a direction substantially parallel to a direction of the channel; and
the detector comprises a plurality of detectors that each correspond to one of the ICE cores.

11. A microfluidic optical computing device as defined in claim 10, wherein the electromagnetic radiation source comprises a plurality of electromagnetic radiation sources that each correspond to one of the detectors.

12. A microfluidic optical computing device as defined in claim 1, wherein:
the device substrate comprises a first exterior surface and a second exterior surface opposite the first exterior surface;
the channel extends through the device substrate in a direction substantially parallel to the first and second exterior surfaces;
the electromagnetic radiation source is positioned along the second exterior surface, the electromagnetic radiation source comprising a plurality of electromagnetic radiation sources;
the detector is positioned along the second exterior surface, the detector comprising a plurality of detectors;
the electromagnetic radiation sources and the detectors being positioned side-by-side in an alternating fashion;
the multivariate optical computing device further comprising an Integrated Computational Element ("ICE") core positioned on the device substrate, the ICE core comprising a plurality of ICE cores positioned side-by-side such that a void region is positioned between two ICE cores;
the channel comprises a reflector positioned along a side of the channel that is opposite the second exterior surface;
the electromagnetic radiation sources are positioned adjacent the void regions such that the electromagnetic radiation passes through the void regions to optically interact with the fluid sample, the reflector reflecting the sample-interacted light back toward the ICE cores; and
each detector is substantially aligned with one of the ICE cores to receive the optically-interacted light.

13. A microfluidic optical computing device as defined in claim 1, further comprising a matrix of channels within the device substrate.

14. A microfluidic optical computing device as defined in claim 1, further comprising a signal processor communicably coupled to the multivariate optical calculation device to determine the at least one property of the fluid sample.

15. A microfluidic optical computing device as defined in claim 1, wherein the microfluidic optical computing device is positioned along a pipeline or wellbore.

16. An optical computing method utilizing a microfluidic optical computing device as described in any of claims 1-9 and 11-14.

17. An optical computing method as defined in claim 16, further comprising deploying the microfluidic optical computing device into a wellbore or pipeline.

18. An optical computing method as defined in claim 16, further comprising performing a pressure-volume-temperature analysis based upon the signal.

19. An optical computing device, comprising:
a device substrate having a matrix of channels therein to receive a fluid samples; and
a multivariate optical calculation device positioned to perform a regression calculation on light emanating from the fluid samples within the channels to thereby produce signals which correspond to at least one property of the fluid samples, wherein the multivariate optical calculation device is integrated into the device substrate.

20. An optical computing device as defined in claim 19, wherein:
the device is microfluidic; and
a plurality of Integrated Computational Element ("ICE") cores are positioned on the device substrate in order to perform the regression calculation.

* * * * *

UNITED STATES PATENT AND TRADEMARK OFFICE
CERTIFICATE OF CORRECTION

PATENT NO. : 10,613,073 B2
APPLICATION NO. : 14/426689
DATED : April 7, 2020
INVENTOR(S) : David L. Perkins and Christopher Michael Jones Page 1 of 1

It is certified that error appears in the above-identified patent and that said Letters Patent is hereby corrected as shown below:

In the Specification

In Column 4, Line 6: "Mofluidic" should be Microfluidic.

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*